(12) United States Patent
Uda et al.

(10) Patent No.: US 10,040,863 B2
(45) Date of Patent: Aug. 7, 2018

(54) ANTICANCER AGENT

(71) Applicant: Japan Science and Technology Agency, Kawaguchi-shi, Saitama (JP)

(72) Inventors: Taizo Uda, Oita (JP); Emi Hifumi, Oita (JP)

(73) Assignee: JAPAN SCIENCE AND TECHNOLOGY AGENCY, Kawaguchi-Shi (JP)

( * ) Notice: Subject to any disclaimer, the term of this patent is extended or adjusted under 35 U.S.C. 154(b) by 96 days.

(21) Appl. No.: 15/166,647

(22) Filed: May 27, 2016

(65) Prior Publication Data

US 2016/0340441 A1 Nov. 24, 2016

Related U.S. Application Data

(62) Division of application No. 14/383,118, filed as application No. PCT/JP2013/055927 on Mar. 5, 2013.

(30) Foreign Application Priority Data

Mar. 8, 2012 (JP) ................................ 2012-052334

(51) Int. Cl.
   *C07K 16/30* (2006.01)
   *C07K 16/18* (2006.01)
   *A61K 39/00* (2006.01)

(52) U.S. Cl.
   CPC .......... *C07K 16/3023* (2013.01); *C07K 16/18* (2013.01); *A61K 2039/505* (2013.01); *C07K 2317/21* (2013.01); *C07K 2317/515* (2013.01); *C07K 2317/60* (2013.01); *C07K 2317/73* (2013.01)

(58) Field of Classification Search
   None
   See application file for complete search history.

(56) References Cited

U.S. PATENT DOCUMENTS

| 2003/0105000 A1 | 6/2003 | Pero et al. |
| 2012/0322135 A1 | 12/2012 | Uda et al. |

FOREIGN PATENT DOCUMENTS

| JP | 2005-508176 A | 3/2005 |
| JP | 2006-501856 A | 1/2006 |
| JP | 2006-197930 A | 8/2006 |
| JP | 2011-521647 A | 7/2011 |
| JP | 2011-526480 A | 10/2011 |
| WO | 2004/033658 A2 | 4/2004 |
| WO | 2008/029807 A1 | 3/2008 |
| WO | 2009/100110 A1 | 8/2009 |
| WO | 2009/155015 A1 | 12/2009 |
| WO | 2011/102517 A1 | 8/2011 |

OTHER PUBLICATIONS

Japanese Patent Office, "International Search Report," issued in International Application No. PCT/JP2013/055927, dated May 7, 2013.
Derry C. Roopenian, et al., "FcRn: the neonatal Fc receptor comes of age," Nature Reviews Immunology, vol. 7, p. 715-725 (Sep. 2007).
Japanese Patent Office, "Notice of Reasons for Rejection," issued in JP 2013-544897, dated Nov. 19, 2013.
Gulshat T. Ibragimova and Rebecca C. Wade, "Stability of the Beta-Sheet of the WW Domain: A Molecular Dynamics Simulation Study", Biophysical Journal, vol. 77, pp. 2191-2198 (1999).
Naoko Fujimoto et al., "Characteristic features of human catalytic light chain, 22F6, showing the suppression of influenza virus infection by the different way", FASEB Journal, vol. 24 (Apr. 2010), Abstract presented at Conference on Experimental Biology, Anaheim, CA, USA, Apr. 24-28, 2010, American Association of Anatomists, American Physiological Society, American Society for Biochemistry and Molecular Biology, Accession No. 2013:69168 BIOSIS, Document No. PREV201300069168.
J.M. Colman, "Effects of amino acid sequence changes on antibody-antigen interactions", Research in Immunology, vol. 145, Issue 1, pp. 33-36 (1994).
Stuart Rudikoff et al., "Single amino acid substitution altering antigen-binding specificity", Proceedings of the National 4cademy of Sciences USA (PNAS), vol. 79, No. 6, pp. 1979-1983 (Mar. 1982), Immunology.
Jeffrey Skolnick and Jacquelyn S. Fetrow, "From genes to protein structure and function: novel applications of computational approaches in the genomic era", Trends in Biotechnology, vol. 18, Issue 1, pp. 34-39 (Jan. 2000).
United States Patent and Trademark Office, "Restriction Requirement", issued in U.S. Appl. No. 14/383,118, dated Dec. 17, 2015.
United States Patent and Trademark Office, "Non-Final Office Action", issued in U.S. Appl. No. 14/383,118, dated Mar. 2, 2016.

*Primary Examiner* — Peter J Reddig

(57) ABSTRACT

According to the present invention, an anticancer agent is provided that has as an active ingredient thereof a human antibody light chain that demonstrates cytotoxicity against cancer cells and particularly lung cancer cells. The anticancer agent of the present invention primarily comprises: a human antibody κ-type light chain in the form of a dimer in which the variable region is composed of a polypeptide represented by the amino acid sequence of SEQ ID NO: 1, 9 or 13 or an amino acid sequence in which one or a plurality of amino acids have been added, deleted or substituted in these amino acid sequences; or, a human antibody κ-type light chain in the form of a monomer in which the variable region is composed of a polypeptide represented by the amino acid sequence of SEQ ID NO: 19 or an amino acid sequence in which one or a plurality of amino acids have been added, deleted or substituted in the amino acid sequence.

5 Claims, 14 Drawing Sheets

FIG. 1

```
                    VARIABLE REGION        CDR1                                              CDR2
#1-4   (A18b)       DVVMTQTPLSLSVTPGQPASISCKSSQSLLHSDGKT-YLYWYLQKPGHSPHLLIYEVSS 58
#2-3   (A3/A19)     DVVMTQSPLSLPVTPGEPASISCRSSQSLLYGNGNN-YLDWYLQKPGQSPQLLIYLGSI 58
#4-1   (02/01)      DVVMTQTPLSLSVTPGEPASISCRSTQSLLDSDGVNPSFDWYVQKPGQSPQLLIHRGFY 59
#7-2   (A3/A19)     DVVMTQSPLSLPVTPGEPASISCRSSQSLLHSNGYN-YLDWYLQKPGQSPQLLIYLGSN 58
#8-2   (A18b)       DVVMTQTPLSLSVTPGQPASLSCKSSQSLLHSDGKT-YLYWYLQKPGQSPQLLIYEVSS 58
#9a-2  (A18b)       DVVMTQTPLSLSVTPGQPASISCKSSQSLLHSDGKT-YLYWYLQKPGQSPQLLIYEVSS 58
#11-1  (A18b)       DIVMTQTPLSLSVTPGQPASISCKSSQSLLHSDGKT-YLYWYLQKPGQSPQLLIYEVSS 58
#13-1  (A3/A19)     DVVMTQSPLSLPVTPGEPASISCRSSQSLLHSNGYN-YLDWYLQKPGQSPQLLIYLGSN 58
#14-1  (A3/A19)     DIVMTQSPLSLPVTPGEPASISCRSSQSLLHSNGYN-YLDWYLQKPGQSPQLLIYLGSN 58
22F6-4 (A3/A19)     DIVMTQSPLSLPVTPGEPASISCRSSQSLLHSNGFN-YLDWYLQKPGQSPQLLIYEGST 58
23D4-1 (A3/A19)     DIVMTQSPLSLPVTPGEPASISCRSSQSLLHSNGYN-YLDWYLQKPGQSPQLLIYEGSN 58
                    *:****:***,.**.*:.**:** *:***:.:*.   :  *  *:.   *:

CDR3         CONSTANT REGION
#1-4   (A18b)       RFSGVPDRFSGSGSGTDFTLKISRVEAEDVGVYYCMQGLHLPQYTFGQGTKLEIKRTVAA 118
#2-3   (A3/A19)     RASGVPDRFSGSGSGTDFQLKISRVEADDVGIYYCMQAQQGP-PTFGGGTKVEIKRTVAA 118
#4-1   (02/01)      RASGVPDRFSGSGSGTDFTLRISRVEAEDVGVYYCMQRIEFP-LTFGGGTKVEIKRTVAA 118
#7-2   (A3/A19)     RASGVPDRFSGSGSGTDFTLKISRVEAEDVGVYYCMQALQTP-RTFGQGTKVEIKRTVAA 117
#8-2   (A18b)       RFSGVPDRFSGSGSGTDFTLKISRVEAEDVGVYYCMEGTHLP-WTFGQGTKVEIKRTVAA 117
#9a-2  (A18b)       RFSGVPDRFSGSGSGTDFTLKISRVEAEDVGVYYCMQGIHLP-YTFGQGTKLEIKRTVAA 117
#11-1  (A18b)       RFSGVPDRFSGSGSGTDFTLKISRVEAEDVGVYYCMQGIHLR-YTFGQGTKLEIKRTVAA 117
#13-1  (A3/A19)     RASGVPDRFSGSGSGTDFTLKISRVEAEDVGVYYCMQALQTPPWTFGQGTKVEIKRTVAA 118
#14-1  (A3/A19)     RASGVPDRFSGSGSGTDFTLKISRVEAEDVGVYYCMQALQTP-RTFGQGTKLEIKRTVAA 117
22F6-4 (A3/A19)     RASGVPDRFSGSGSGTDFTLRISRVEAEDVGVYFCMQAVQTP-FTFGPGTRLDIKRTVAA 118
23D4-1 (A3/A19)     RASGVPDRFSGSGSGTDFTLKISRVEAEDVGVYYCMQALQTP-WTFGQGTKVEIKRTVAA 118
                    * ******.**,:***.*.**:***:*.*:**:       *** **::: ******

#1-4   (A18b)       PSVFIFPPSDEQLKSGTASVVCLLNNFYPREAKVQWKVDNALQSGNSQESVTEQDSKDST 178
#2-3   (A3/A19)     PSVFIFPPSDEQLKSGTASVVCLLNNFYPREAKVQWKVDNALQSGNSQESVTEQDSKDST 177
#4-1   (02/01)      PSVFIFPPSDEQLKSGTASVVCLLNNFYPREAKVQWKVDNALQSGNSQESVTEQDSKDST 178
#7-2   (A3/A19)     PSVFIFPPSDEQLKSGTASVVCLLNNFYPREAKVQWKVDNALQSGNSQESVTEQDSKDST 177
#8-2   (A18b)       PSVFIFPPSDEQLKSGTASVVCLLNNFYPREAKVQWKVDNALQSGNSQESVTEQDSKDST 177
#9a-2  (A18b)       PSVFIFPPSDEQLKSGTASVVCLLNNFYPREAKVQWKVDNALQSGNSQESVTEQDSKDST 177
#11-1  (A18b)       PSVFIFPPSDEQLKSGTASVVCLLNNFYPREAKVQWKVDNALQSGNSQESVTEQDSKDST 177
#13-1  (A3/A19)     PSVFIFPPSDEQLKSGTASVVCLLNNFYPREAKVQWKVDNALQSGNSQESVTEQDSKDST 178
#14-1  (A3/A19)     PSVFIFPPSDEQLKSGTASVVCLLNNFYPREAKVQWKVDNALQSGNSQESVTEQDSKDST 177
22F6-4 (A3/A19)     PSVFIFPPSDEQLKSGTASVVCLLNNFYPREAKVQWKVDNALQSGNSQESVTEQDSKDST 177
23D4-1 (A3/A19)     PSVFIFPPSDEQLKSGTASVVCLLNNFYPREAKVQWKVDNALQSGNSQESVTEQDSKDST 177
                    ************************************************************

#1-4   (A18b)       YSLSSTLTLSKADYEKHKLYACEVTHQGLSSPVTKSFNRGEC 220
#2-3   (A3/A19)     YSLSSTLTLSKADYEKHKLYACEVTHQGLSSPVTKSFNRGEC 219
#4-1   (02/01)      YSLSSTLTLSKADYEKHKLYACEVTHQGLSSPVTKSFNRGEC 220
#7-2   (A3/A19)     YSLSSTLTLSKADYEKHKLYACEVTHQGLSSPVTKSFNRGEC 219
#8-2   (A18b)       YSLSSTLTLSKADYEKHKLYACEVTHQGLSSPVTKSFNRGEC 219
#9a-2  (A18b)       YSLSSTLTLSKADYEKHKLYACEVTHQGLSSPVTKSFNRGEC 219
#11-1  (A18b)       YSLSSTLTLSKADYEKHKLYACEVTHQGLSSPVTKSFNRGEC 219
#13-1  (A3/A19)     YSLSSTLTLSKADYEKHKLYACEVTHQGLSSPVTKSFNRGEC 220
#14-1  (A3/A19)     YSLSSTLTLSKADYEKHKLYACEVTHQGLSSPVTKSFNRGEC 219
22F6-4 (A3/A19)     YSLSSTLTLSKADYEKHKVYACEVTHQGLSSPVTKSFNRGEC 219
23D4-1 (A3/A19)     YSLSSTLTLSKADYEKHKVYACEVTHQGLSSPVTKSFNRGEC 219
                    *****************:***********************
```

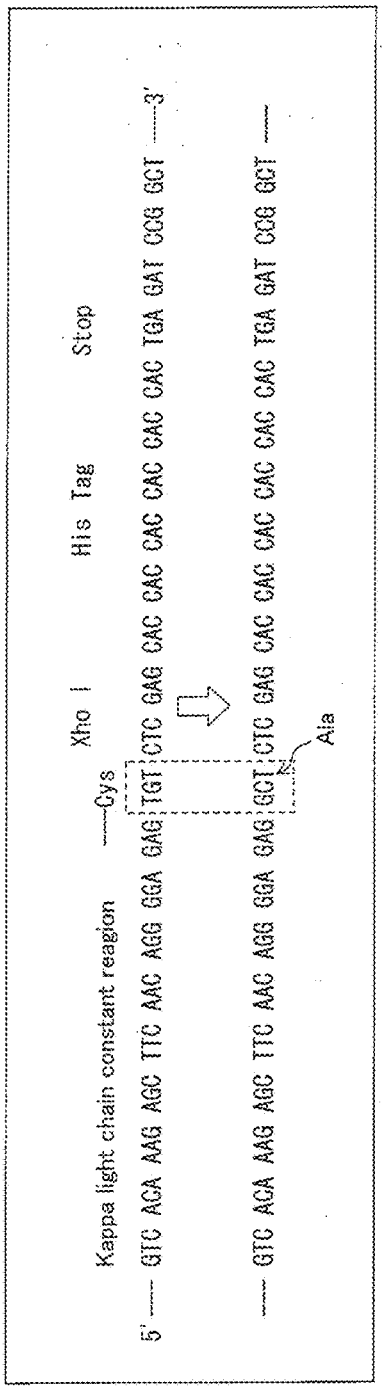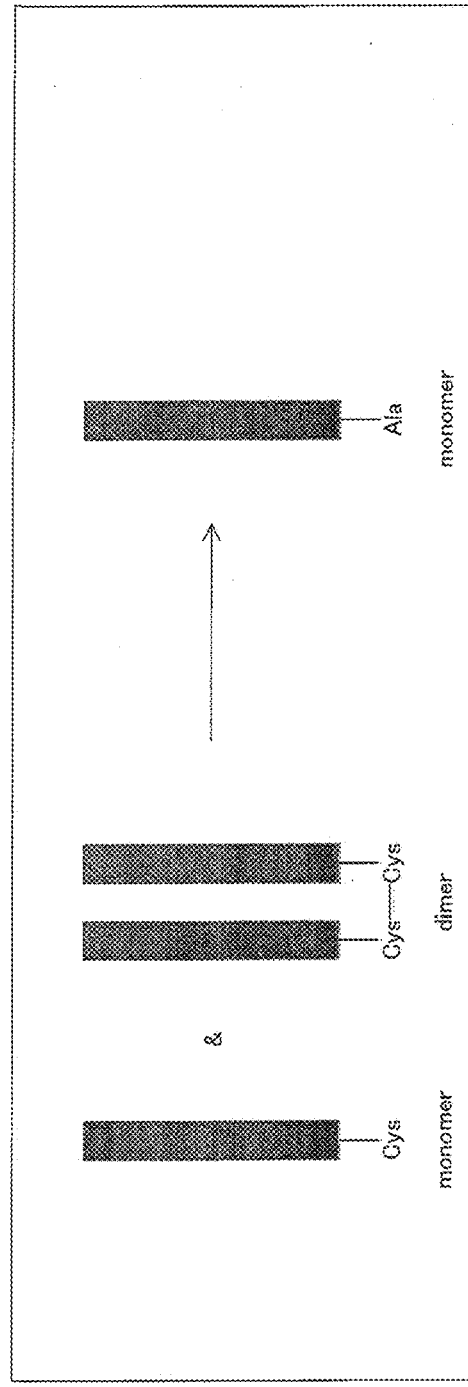

```
                    ----------+---------+---------+---------+---------+
                             10        20        30        40        50
                    ----------+---------+---------+---------+---------+
#1H31YC220A.pro     DVVMTQTPLSLSVTPGQPASISCKSSQSLLYSDGKTYLYWYLQKPGHSPH       50
#7VL(I).pro         EIVMTQSPLSLPVTPGEPASISCRSSQSLLHSNTRNYLDWYLQKPGQSPQ       50
#7RLI.pro           EIVMTQSPLSLPVTPGEPASISCRSSQSLLHSNTRNYLDWYLQKPGQSPQ       50
C51.pro             EIVLTQSPATLSLSPGERATLSCRASQSV-----SSYLAWYQQKPGQAPR       45
C87.pro             EIVLTQSPATLSLSPGERATFSCRASQSL-----SSYVAWYQKKPGQAPR       45

----------+---------+---------+---------+---------+
                             60        70        80        90       100
                    ----------+---------+---------+---------+---------+
#1H31YC220A.pro     LLIYEVSSRFSGVPDRFSGSGSGTDFTLKISRVEAEDVGVYYCMQGLHL-       99
#7VL(I).pro         LLIYLGSNRASGVPDRFSGSGSGTDFTLKISRVEAEDVGVYYCMQGLQT-       99
#7RLI.pro           LLIYLGSNRASGVPDRFSGSGSGTDFTLKISRVEAEDVGVYYCMQGLQT-       99
C51.pro             LLIYDASNRATGIPARFSGSGSGTDFTLTITSLEPEDFAVYYCQQR-SDW       94
C87.pro             LLIYDTSTRAAGIPARFSGGGSGTDFTLTISSLEPEDCAVYYCQRR-AT-       93

----------+---------+---------+---------+---------+
                            110       120       130       140       150
                    ----------+---------+---------+---------+---------+
#1H31YC220A.pro     PQYTFGQGTKLEIKRTVAAPSVFIFPPSDEQLKSGTASVVCLLNNFYPRE      149
#7VL(I).pro         PI-TFGQGTKVEIKRTVAAPSVFIFPPSDEQLKSGTASVVCLLNNFYPRE      148
#7RLI.pro           PI-TFGQGTRLEIKRTVAAPSVFIFPPSDEQLKSGTASVVCLLNNFYPRE      148
C51.pro             PL-TFGGGTKVEIKRTVAAPSVFIFPPSDEQLKSGTASVVCLLNNFYPRE      143
C87.pro             PY-TFGQGTRLEIKRTVAAPSVFIFPPSDEQLKSGTASVVCLLNNFYPRE      142

----------+---------+---------+---------+---------+
                            160       170       180       190       200
                    ----------+---------+---------+---------+---------+
#1H31YC220A.pro     AKVQWKVDNALQSGNSQESVTEQDSKDSTYSLSSTLTLSKADYEKHKLYA      199
#7VL(I).pro         AKVQWKVDNALQSGNSQESVTEQDSKDSTYSLSSTLTLSKADYEKHKLYA      198
#7RLI.pro           AKVQWKVDNALQSGNSQESVTEQDSKDSTYSLSSTLTLSKADYEKHKLYA      198
C51.pro             AKVQWKVDNALQSGNSQESVTEQDSKDSTYSLSSTLTLSKADYEKHKVYA      193
C87.pro             AKVQWKVDNALQSGNSQESVTEQDSKDSTYSLSSTLTLSKADYEKHRVYA      192

----------+---------+--
                            210       220
                    ----------+---------+--
#1H31YC220A.pro     CEVTHQGLSSPVTKSFNRGEA                                   220
#7VL(I).pro         CEVTHQGLSSPVTKSFNRGEC                                   219
#7RLI.pro           CEVTHQGLSSPVTKSFNRGEC                                   219
C51.pro             CEVTHQGLSSPVTKSFNRGEC                                   214
C87.pro             CEVTHQGLSSPVTKSFNRGEC                                   213
```

FIG. 6B

MOLT-4

```
              10         20         30         40         50
              |----+----|----+----|----+----|----+----|----+----|

#1H31YC220A.pro  DVVMTQTPLSLSVTPGQPASISCKSSQSLLYSDG-KTYLYWYLQKPGHSP   49
#4.pro           DVVMTQTPLSLSVTPGEPASISCRSTQSLLDSDGVNPSFDWYVQKPGQSP   50
#7EI.pro         EIVMTQSPLSLPVTPGEPASISCRSSQSLLHSNG-YNYLDWYLQKPGQSP   49
#7TR.pro         DVVMTQSPLSLPVTPGEPASISCRSSQSLLHSNT-RNYLDWYLQKPGQSP   49
#7RLI.pro        EIVMTQSPLSLPVTPGEPASISCRSSQSLLHSNT-RNYLDWYLQKPGQSP   49
#7VL.pro         EIVMTQSPLSLPVTPGEPASISCRSSQSLLHSNT-RNYLDWYLQKPGQSP   49
S13.pro          DIVMTQSPLSLPVTPGEPASISCRSSQSLLHSNG-YNYLDWYLQKPGQSP   49
S21.pro          DIVMTQSPLSLPVTPGEPASISCRSSQSLLHSNG-YNYLDWYLQKPGQSP   49
S38.pro          DIVMTQSPLSLPVTPGEPASISCRSSQSLLHSNG-YNYLDWYLQKPGQSP   49
C51.pro          EIVLTQSPATLSLSPGERATLSCRASQS------VSSYLAWYQQKPGQAP   44

60         70         80         90        100
              |----+----|----+----|----+----|----+----|----+----|

#1H31YC220A.pro  HLLIYEVSSRFSGVPDRFSGSGSGTDFTLKISRVEAEDVGVYYCMQGLHL   99
#4.pro           QLLIHRGFYRASGVPDRFSGSGSGTDFTLKISRVEAEDVGVYYCMQRIEF  100
#7EI.pro         QLLIYLGSNRASGVPDRFSGSGSGTDFTLKISRVEAEDVGVYYCMQALQT   99
#7TR.pro         QLLIYLGSNRASGVPDRFSGSGSGTDFTLKISRVEAEDVGVYYCMQALQT   99
#7RLI.pro        QLLIYLGSNRASGVPDRFSGSGSGTDFTLKISRVEAEDVGVYYCMQGLQT   99
#7VL.pro         QLLIYLGSNRASGVPDRFSGSGSGTDFTLKISRVEAEDVGVYYCMQALQT   99
S13.pro          QLLIYLGSNRDSGVPDRFSGSGSGTDFTLKISSVEAEDVGVYYCMQALET   99
S21.pro          QLLIYLGSNRASGVPDRFSGSGSGTDFTLKISRVEAEDVGVYYCMQALQT   99
S38.pro          QLLIYLGSNRASGVPDRFSGSGSGTDFTLKISRVEAEDVGVYYCMQALQT   99
C51.pro          RLLIYDASNRATGIPARFSGSGSGTDFTLTITSLEPEDFAVYYCQQRSDW   94

110        120        130        140        150
              |----+----|----+----|----+----|----+----|----+----|

#1H31YC220A.pro  PQYTFGQGTKLEIKRTVAAPSVFIFPPSDEQLKSGTASVVCLLNNFYPRE  149
#4.pro           PL-TFGGGTKVEIKRTVAAPSVFIFPPSDEQLKSGTASVVCLLNNFYPRE  149
#7EI.pro         PR-TFGQGTKVEIKRTVAAPSVFIFPPSDEQLKSGTASVVCLLNNFYPRE  148
#7TR.pro         PR-TFGQGTKVEIKRTVAAPSVFIFPPSDEQLKSGTASVVCLLNNFYPRE  148
#7RLI.pro        PI-TFGQGTRLEIKRTVAAPSVFIFPPSDEQLKSGTASVVCLLNNFYPRE  148
#7VL.pro         PR-TFGQGTKVEIKRTVAAPSVFIFPPSDEQLKSGTASVVCLLNNFYPRE  148
S13.pro          PP-TFGQGTKLEIKRTVAAPSVFIFPPSDEQLKSGTASVVCLLNNFYPRE  148
S21.pro          PR-TFGPGTKVDIKRTVAAPSVFIFPPSDEQLKSGTASVVCLLNNFYPRE  148
S38.pro          -Y-TFGQGTKLEIKRTVAAPSVFIFPPSDEQLKSGTASVVCLLNNFYPRE  147
C51.pro          PL-TFGGGTKVEIKRTVAAPSVFIFPPSDEQLKSGTASVVCLLNNFYPRE  143

160        170        180        190        200
              |----+----|----+----|----+----|----+----|----+----|

#1H31YC220A.pro  AKVQWKVDNALQSGNSQESVTEQDSKDSTYSLSSTLTLSKADYEKHKLYA  199
#4.pro           AKVQWKVDNALQSGNSQESVTEQDSKDSTYSLSSTLTLSKADYEKHKLYA  199
#7EI.pro         AKVQWKVDNALQSGNSQESVTEQDSKDSTYSLSSTLTLSKADYEKHKLYA  198
#7TR.pro         AKVQWKVDNALQSGNSQESVTEQDSKDSTYSLSSTLTLSKADYEKHKLYA  198
#7RLI.pro        AKVQWKVDNALQSGNSQESVTEQDSKDSTYSLSSTLTLSKADYEKHKLYA  198
#7VL.pro         AKVQWKVDNALQSGNSQESVTEQDSKDSTYSLSSTLTLSKADYEKHKLYA  198
S13.pro          AKVQWKVDNALQSGNSQESVTEQDSKDSTYSLSSTLTLSKADYEKHKVYA  198
S21.pro          AKVQWKVDNALQSGNSQESVTEQDSKDSTYSLSSTLTLSKADYEKHKVYA  198
S38.pro          AKVQWKVDNALQSGNSQESVTEQDSKDSTYSLSSTLTLSKADYEKHKVYA  197
C51.pro          AKVQWKVDNALQSGNSQESVTEQDSKDSTYSLSSTLTLSKADYEKHKVYA  193
```

*FIG. 6C*

```
                         ----------+----------+-
                             210        220
                         ----------+----------+-
#1H31YC220A.pro          CEVTHQGLSSPVTKSFNRGEA                  220
#4.pro                   CEVTHQGLSSPVTKSFNRGEC                  220
#7EI.pro                 CEVTHQGLSSPVTKSFNRGEC                  219
#7TR.pro                 CEVTHQGLSSPVTKSFNRGEC                  219
#7RLI.pro                CEVTHQGLSSPVTKSFNRGEC                  219
#7VL.pro                 CEVTHQGLSSPVTKSFNRGEC                  219
S13.pro                  CEVTHQGLSSPVTKSFNRGEC                  219
S21.pro                  CEVTHQGLSSPVTKSFNRGEC                  219
S38.pro                  CEVTHQGLSSPVTKSFNRGEC                  218
C51.pro                  CEVTHQGLSSPVTKSFNRGEC                  214
```

```
              ---------+---------+---------+---------+---------+
                      10        20        30        40        50
              ---------+---------+---------+---------+---------+
#1H31YC220A.pro DVVMTQTPLSLSVTPGQPASISCKSSQSLLYSDG-KT-YLYWYLQKPGHS
#4.pro          DVVMTQTPLSLSVTPGEPASISCRSTQSLLDSDGVNP-SFDWYVQKPGQS
#7.pro          DVVMTQSPLSLPVTPGEPASISCRSSQSLLHSNG-YN-YLDWYLQKPGQS
#7RLI.pro       EIVMTQSPLSLPVTPGEPASISCRSSQSLLHSNT-RN-YLDWYLQKPGQS
#10.pro         DVVMTQTPLSLSVTPGQPASISCKSSQSLLHSDG-KT-YFYWYLQRPGRS
#11.pro         DIVMTQTPLSLSVTPGQPASISCKSSQSLLHSDG-KT-YLYWYLQKPGQS
22F6.pro        DIVMTQSPLSLPVTPGEPASISCRSSQSLLHSNG-FN-YLDWYLQKPGQS
22F6C220A.pro   DIVMTQSPLSLPVTPGEPASISCRSSQSLLHSNG-FN-YLDWYLQKPGQS
C51.pro         EIVLTQSPATLSLSPGERATLSCRASQS------VSS-YLAWYQQKPGQA
C67.pro         EIVLTQSPGTLSLSPGERATLSCRASQS------VSSSNLAWYQQKPGQA
C82.pro         EIVLTQSPATLSLSPGERATLSCRASQS------VGP-FLAWYQQKPGQA
C88.pro         EIVLTQSPATLSLSPGERATLSCRASES------VSG-YLAWYQQKPGQA ---------+---------+---------+---------+---------+
                      60        70        80        90       100
              ---------+---------+---------+---------+---------+
#1H31YC220A.pro PHLLIYEVSSRFSGVPDRFSGSGSGTDFTLKISRVEAEDVGVYYCMQ--G
#4.pro          PQLLIHRGFYRASGVPDRFSGSGSGTDFTLRISRVEAEDVGVYYCMQ--R
#7.pro          PQLLIYLGSNRASGVPDRFSGSGSGTDFTLKISRVEAEDVGVYYCMQ--A
#7RLI.pro       PQLLIYLGSNRASGVPDRFSGSGSGTDFTLKISRVEAEDVGVYYCMQ--G
#10.pro         PQLLIQEVSRRFSGVPDRFSGSGSGSDFTLKISRVEAEDVGVYYCMQ--G
#11.pro         PQLLIYEVSSRFSGVPDRFSGSGSGTDFTLKISRVEAEDVGVYYCMQ--G
22F6.pro        PQLLIYLGSTRASGVPDRFSGSGSGTDFTLRISRVEAEDVGVYFCMQ--A
22F6C220A.pro   PQLLIYLGSTRASGVPDRFSGSGSGTDFTLRISRVEAEDVGVYFCMQ--A
C51.pro         PRLLIYDASNRATGIPARFSGSGSGTDFTLTITSLEPEDFAVYYCQQ--R
C67.pro         PRLLIYGASSRATGIPDRFSGSGSGTDYTLTISRLEPEDFALYYCQQYGS
C82.pro         PRLLIYDTSTRATGIPARFSGSGSGTDFTLTISSLEPEDFAVYYCQQ--R
C88.pro         PRLLIYEASNRATGIPARFSGSGSGPDFTLTISSLEPEDFAFYYCQQ--R
```

FIG. 6E

```
              ----------+----------+----------+----------+----------+
                     110        120        130        140        150
              ----------+----------+----------+----------+----------+
#1H31YC220A.pro LHLP---QYTFGQGTKLEIKRTVAAPSVFIFPPSDEQLKSGTASVVCLLN
#4.pro          IEFP----LTFGGGTKVEIKRTVAAPSVFIFPPSDEQLKSGTASVVCLLN
#7.pro          LQTP----RTFGQGTKVEIKRTVAAPSVFIFPPSDEQLKSGTASVVCLLN
#7RLI.pro       LQTP----ITFGQGTRLEIKRTVAAPSVFIFPPSDEQLKSGTASVVCLLN
#10.pro         TYVP----HTFGQGTKVEIKRTVAAPSVFIFPPSDEQLKSGTASVVCLLN
#11.pro         IHLP----YTFGQGTKLEIKRTVAAPSVFIFPPSDEQLKSGTASVVCLLN
22F6.pro        VQTP----FTFGPGTRLDIKRTVAAPSVFIFPPSDEQLKSGTASVVCLLN
22F6C220A.pro   VQTP----FTFGPGTRLDIKRTVAAPSVFIFPPSDEQLKSGTASVVCLLN
C51.pro         SDWP----LTFGGGTKVEIKRTVAAPSVFIFPPSDEQLKSGTASVVCLLN
C67.pro         SLW------TFGQGTKVEIKRTVAAPSVFIFPPSDEQLKSGTASVVCLLN
C82.pro         YTWP--G-NSFGGGAKVEIKRTVAAPSVFIFPPSDEQLKSGTASVVCLLN
C88.pro         SNWPPR--STFGQGTRLEMKRTVAAPSVFIFPPSDEQLKSGTASVVCLLN ----------+----------+----------+----------+----------+
                     160        170        180        190        200
              ----------+----------+----------+----------+----------+
#1H31YC220A.pro NFYPREAKVQWKVDNALQSGNSQESVTEQDSKDSTYSLSSTLTLSKADYE
#4.pro          NFYPREAKVQWKVDNALQSGNSQESVTEQDSKDSTYSLSSTLTLSKADYE
#7.pro          NFYPREAKVQWKVDNALQSGNSQESVTEQDSKDSTYSLSSTLTLSKADYE
#7RLI.pro       NFYPREAKVQWKVDNALQSGNSQESVTEQDSKDSTYSLSSTLTLSKADYE
#10.pro         NFYPREAKVQWKVDNALQSGNSQESVTEQDSKDSTYSLSSTLTLSKADYE
#11.pro         NFYPREAKVQWKVDNALQSGNSQESVTEQDSKDSTYSLSSTLTLSKADYE
22F6.pro        NFYPREAKVQWKVDNALQSGNSQESVTEQDSKDSTYSLSSTLTLSKADYE
22F6C220A.pro   NFYPREAKVQWKVDNALQSGNSQESVTEQDSKDSTYSLSSTLTLSKADYE
C51.pro         NFYPREAKVQWKVDNALQSGNSQESVTEQDSKDSTYSLSSTLTLSKADYE
C67.pro         NFYPREAKVQWKVDNALQSGNSQESVTEQDSKDSTYSLSSTLTLSKADYE
C82.pro         NFYPREAKVQWKVDNALQSGNSQESVTEQDSKDSTYSLSSTLTLSKADYE
C88.pro         NFYPREAKVQWKVDNALQSGNSQESVTEQDSKDSTYSLSSTLTLSKADYE
```

*FIG. 6F*

```
                        ----------+----------+--------
                                 210        220
                        ----------+----------+--------
#1H31YC220A.pro         KHKLYACEVTHQGLSSPVTKSFNRGEA
#4.pro                  KHKLYACEVTHQGLSSPVTKSFNRGEC
#7.pro                  KHKLYACEVTHQGLSSPVTKSFNRGEC
#7RLI.pro               KHKLYACEVTHQGLSSPVTKSFNRGEC
#10.pro                 KHKLYACEVTHQGLSSPVTKSFNRGEC
#11.pro                 KHKLYACEVTHQGLSSPVTKSFNRGEC
22F6.pro                KHKVYACEVTHQGLSSPVTKSFNRGEC
22F6C220A.pro           KHKVYACEVTHQGLSSPVTKSFNRGEA
C51.pro                 KHKVYACEVTHQGLSSPVTKSFNRGEC
C67.pro                 KHKVYACEVTHQGLSSPVTKSFNRGEC
C82.pro                 KHKVYACEVTHQGLSSPVTKSFNRGEC
C88.pro                 KHKVYACEVTHQGLSSPVTKSFNRGEC
```

*FIG. 6G*

BxPC-3

```
               ----------+---------+---------+---------+---------+
                    10        20        30        40        50
               ----------+---------+---------+---------+---------+
#4.pro         DVVMTQTPLSLSVTPGEPASISCRSTQSLLDSDGVNPSFDWYVQKPGQSP     50
#7G.pro        DVVMTQSPLSLPVTPGEPASISCRSSQSLLHSNGYN-YLDWYLQKPGQSP     49
#7EI.pro       EIVMTQSPLSLPVTPGEPASISCRSSQSLLHSNGYN-YLDWYLQKPGQSP     49
#7RLI.pro      EIVMTQSPLSLPVTPGEPASISCRSSQSLLHSNTRN-YLDWYLQKPGQSP     49
#7VL.pro       EIVMTQSPLSLPVTPGEPASISCRSSQSLLHSNTRN-YLDWYLQKPGQSP     49
#13.pro        DVVMTQSPLSLPVTPGEPASISCRSSQSLLHSNGYN-YLDWYLQKPGQSP     49
#14.pro        DIVMTQSPLSLPVTPGEPASISCRSSQSLLHSNGYN-YLDWYLQKPGQSP     49
22F6.pro       DIVMTQSPLSLPVTPGEPASISCRSSQSLLHSNGFN-YLDWYLQKPGQSP     49

----------+---------+---------+---------+---------+
                    60        70        80        90       100
               ----------+---------+---------+---------+---------+
#4.pro         QLLIHRGFYRASGVPDRFSGSGSGTDFTLRISRVEAEDVGVYYCMQRIEF    100
#7G.pro        QLLIYLGSNRASGVPDRFSGSGSGTDFTLKISRVEAEDVGVYYCMQGLQT     99
#7EI.pro       QLLIYLGSNRASGVPDRFSGSGSGTDFTLKISRVEAEDVGVYYCMQALQT     99
#7RLI.pro      QLLIYLGSNRASGVPDRFSGSGSGTDFTLKISRVEAEDVGVYYCMQGLQT     99
#7VL.pro       QLLIYLGSNRASGVPDRFSGSGSGTDFTLKISRVEAEDVGVYYCMQGLQT     99
#13.pro        QLLIYLGSNRASGVPDRFSGSGSGTDFTLKISRVEAEDVGVYYCMQALQT     99
#14.pro        QLLIYLGSNRASGVPDRFSGSGSGTDFTLKISRVEAEDVGVYYCMQALQT     99
22F6.pro       QLLIYLGSTRASGVPDRFSGSGSGTDFTLRISRVEAEDVGVYFCMQAVQT     99

----------+---------+---------+---------+---------+
                   110       120       130       140       150
               ----------+---------+---------+---------+---------+
#4.pro         PL-TFGGGTKVEIKRTVAAPSVFIFPPSDEQLKSGTASVVCLLNNFYPRE    149
#7G.pro        PR-TFGQGTKVEIKRTVAAPSVFIFPPSDEQLKSGTASVVCLLNNFYPRE    148
#7EI.pro       PR-TFGQGTKVEIKRTVAAPSVFIFPPSDEQLKSGTASVVCLLNNFYPRE    148
#7RLI.pro      PI-TFGQGTRLEIKRTVAAPSVFIFPPSDEQLKSGTASVVCLLNNFYPRE    148
#7VL.pro       PR-TFGQGTKVEIKRTVAAPSVFIFPPSDEQLKSGTASVVCLLNNFYPRE    148
#13.pro        PPWTFGQGTKVEIKRTVAAPSVFIFPPSDEQLKSGTASVVCLLNNFYPRE    149
#14.pro        PR-TFGQGTKLEIKRTVAAPSVFIFPPSDEQLKSGTASVVCLLNNFYPRE    148
22F6.pro       PF-TFGPGTRLDIKRTVAAPSVFIFPPSDEQLKSGTASVVCLLNNFYPRE    148

----------+---------+---------+---------+---------+
                   160       170       180       190       200
               ----------+---------+---------+---------+---------+
#4.pro         AKVQWKVDNALQSGNSQESVTEQDSKDSTYSLSSTLTLSKADYEKHKLYA    199
#7G.pro        AKVQWKVDNALQSGNSQESVTEQDSKDSTYSLSSTLTLSKADYEKHKLYA    198
#7EI.pro       AKVQWKVDNALQSGNSQESVTEQDSKDSTYSLSSTLTLSKADYEKHKLYA    198
#7RLI.pro      AKVQWKVDNALQSGNSQESVTEQDSKDSTYSLSSTLTLSKADYEKHKLYA    198
#7VL.pro       AKVQWKVDNALQSGNSQESVTEQDSKDSTYSLSSTLTLSKADYEKHKLYA    198
#13.pro        AKVQWKVDNALQSGNSQESVTEQDSKDSTYSLSSTLTLSKADYEKHKLYA    199
#14.pro        AKVQWKVDNALQSGNSQESVTEQDSKDSTYSLSSTLTLSKADYEKHKLYA    198
22F6.pro       AKVQWKVDNALQSGNSQESVTEQDSKDSTYSLSSTLTLSKADYEKHKVYA    198
```

FIG. 6H

```
                  ----------+---------+--
                         210       220
                  ----------+---------+--
#4.pro      CEVTHQGLSSPVTKSFNRGEC              220
#7G.pro     CEVTHQGLSSPVTKSFNRGEC              219
#7EI.pro    CEVTHQGLSSPVTKSFNRGEC              219
#7RLI.pro   CEVTHQGLSSPVTKSFNRGEC              219
#7VL.pro    CEVTHQGLSSPVTKSFNRGEC              219
#13.pro     CEVTHQGLSSPVTKSFNRGEC              220
#14.pro     CEVTHQGLSSPVTKSFNRGEC              219
22F6.pro    CEVTHQGLSSPVTKSFNRGEC              219
```

```
          ----------+----------+----------+----------+----------+
               10         20         30         40         50
          ----------+----------+----------+----------+----------+
7.pro    DVVMTQSPLSLPVTPGEPASISCRSSQSLLHSNGYNYLDWYLQKPGQSPQ ----------+----------+----------+----------+----------+
               60         70         80         90        100
          ----------+----------+----------+----------+----------+
7.pro    LLIYLGSNRASGVPDRFSGSGSGTDFTLKISRVEAEDVGVYYCMQALQTP ----------+----------+----------+----------+----------+
              110        120        130        140        150
          ----------+----------+----------+----------+----------+
7.pro    RTFGQGTKVEIKRTVAAPSVFIFPPSDEQLKSGTASVVCLLNNFYPREAK ----------+----------+----------+----------+----------+
              160        170        180        190        200
          ----------+----------+----------+----------+----------+
7.pro    VQWKVDNALQSGNSQESVTEQDSKDSTYSLSSTLTLSKADYEKHKLYACE ----------+----------
              210
          ----------+----------
#7.pro    VTHQGLSSPVTKSFNRGEC
```

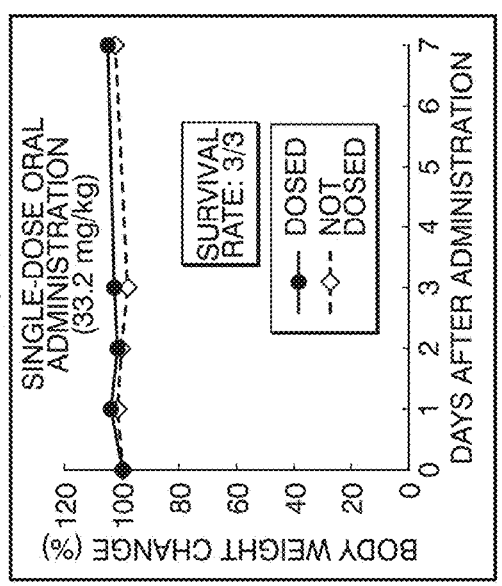

FIG. 8A

SAFETY STUDY OF HUMAN "SUPER ANTIBODY ENZYME" (TOXICITY STUDY)

1. SINGLE-DOSE ORAL DOSE STUDY
   (OBSERVATION PERIOD: 7 DAYS)
2. SINGLE-DOSE INTRAPERITONEAL ACUTE TOXICITY STUDY
   (OBSERVATION PERIOD: 7 DAYS)
3. SINGLE-DOSE INTRAVENOUS ACUTE TOXICITY STUDY
   (OBSERVATION PERIOD: 7 DAYS)
4. 7-DAY REPEAT-DOSE TOXICITY STUDY
5. SINGLE-DOSE INTRAVENOUS TOXICITY STUDY
   (OBSERVATION PERIOD: 28 DAYS)

NO ABNORMALITIES IN ANY OF THE STUDY ANIMALS

FIG. 8B

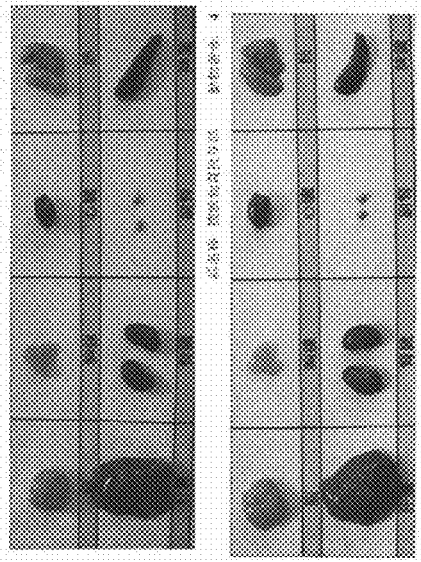

BODY WEIGHT CHANGES IN MICE IN 7-DAY REPEAT-DOSE TOXICITY STUDY (CAUDAL VEIN)

FIG. 8C

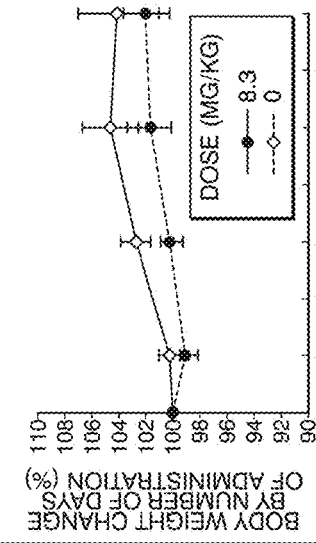

AUTOPSY FINDINGS IN MICE IN 7-DAY REPEAT-DOSE TOXICITY STUDY (CAUDAL VEIN)

ANTICANCER AGENT

CROSS REFERENCE TO RELATED APPLICATIONS

This patent application is a divisional of co-pending U.S. application Ser. No. 14/383,118 having a § 371(c) (1), (2) date of Sep. 5, 2014, which is a U.S. national stage entry under 35 U.S.C. § 371 of International Patent Application No. PCT/JP2013/055927 filed on Mar. 5, 2013, which claims the benefit of foreign priority to Japanese Patent Application No. JP 2012-052334 filed on Mar. 8, 2012, the disclosures of all of which are hereby incorporated by reference in their entireties. The U.S. application Ser. No. 14/383,118 was published on Mar. 5, 2015, as US 2015/0064203 A1, and is now abandoned. The International Application was published in Japanese on Sep. 12, 2013, as International Publication No. WO 2013/133253 A1 under PCT Article 21(2).

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

The sequence listings disclosed in the ASCII text file submitted herewith, named "seqlist.txt" and created on Jan. 25, 2018, the size of which is 74,598 bytes, are hereby incorporated by reference.

TECHNICAL FIELD

The present invention relates to an anticancer agent containing a human antibody κ-type light chain that demonstrates cytotoxicity against cancer cells and particularly lung cancer cells.

The present application claims priority on the basis of Japanese Patent Application No. 2012-52334, filed in Japan on Mar. 8, 2012, the contents of which are incorporated herein by reference.

BACKGROUND ART

Antibodies are composed of heavy chains (H chains) and light chains (L chains). The heavy chains and light chains are composed of a variable region (VR) and a constant region (CR), and the variable region has a complementarity determining region (CDR). Moreover, antibody light chains are classified into κ chains and λ chains.

In recent years, attention has been focused on antibodies having an enzyme-like activity, namely, antibody enzymes. Since antibody enzymes have both the ability of antibodies to accurately recognize molecules and the activity of enzymes, they are expected to be applied in numerous fields, including medicine, the chemical industry and the food industry. In particular, since antibody enzymes exhibit high specificity for a target molecule and are able to impair target molecules due to their enzyme activity, they are expected to serve as superior anticancer agents that demonstrate few adverse side effects.

The inventors of the present invention have heretofore conducted various innovative research on antibody enzymes (see, for example, Patent Document 1). Antibody enzymes having complete human sequences have conventionally been unable to be obtained with the exception of the Bence-Jones Protein (BJP) obtained from multiple myeloma patients. Since there are few multiple myeloma patients and only a small amount of BJP that has enzyme activity, it was difficult to acquire a human antibody enzyme. However, since human antibody enzymes are predicted to demonstrate few adverse side effects when administered to a human body, pharmaceutical companies both at home and overseas are awaiting the development of a useful human antibody enzyme.

PRIOR ART DOCUMENTS

Patent Documents

Patent Document 1: Japanese Unexamined Patent Application, First Publication No. 2006-197930

DISCLOSURE OF THE INVENTION

Problems to be Solved by the Invention

An object of the present invention is to provide an anticancer agent that has for an active ingredient thereof a human antibody light chain that demonstrates cytotoxicity against cancer cells and particularly against lung cancer cells.

Means for Solving the Problems

The inventors of the present invention acquired a novel human antibody light chain from peripheral blood obtained from volunteers hyperimmunized over a plurality of times using a rabies vaccine virus, and as a result of studying those volunteers, surprisingly found that several of the resulting human antibody κ-type light chains demonstrated a high degree of cytotoxicity against cancer cells and particularly lung cancer cells, thereby leading to completion of the present invention.

Namely, the anticancer agent according to the present invention is characterized in that it contains:

(1) a human antibody κ-type light chain in the form of a dimer in which the variable region is composed of a polypeptide represented by the amino acid sequence of SEQ ID NO: 1, an amino acid sequence in which one or a plurality of the amino acids in that amino acid sequence have been substituted, added or deleted, or an amino acid sequence having homology of 95% or more with that amino acid sequence;

(2) a human antibody κ-type light chain in the form of a dimer in which the variable region is composed of a polypeptide represented by the amino acid sequence of SEQ ID NO: 7, an amino acid sequence in which one or a plurality of the amino acids in that amino acid sequence have been substituted, added or deleted, or an amino acid sequence having homology of 95% or more with that amino acid sequence;

(3) a human antibody κ-type light chain in the form of a dimer in which the variable region is composed of a polypeptide represented by the amino acid sequence of SEQ ID NO: 9, an amino acid sequence in which one or a plurality of the amino acids in that amino acid sequence have been substituted, added or deleted, or an amino acid sequence having homology of 95% or more with that amino acid sequence;

(4) a human antibody κ-type light chain in the form of a dimer in which the variable region is composed of a polypeptide represented by the amino acid sequence of SEQ ID NO: 13, an amino acid sequence in which one or a plurality of the amino acids in that amino acid sequence have been substituted, added or deleted, or an amino acid sequence having homology of 95% or more with that amino acid sequence;

(5) a human antibody κ-type light chain in the form of a monomer in which the variable region is composed of a polypeptide represented by the amino acid sequence of SEQ ID NO: 19, an amino acid sequence in which one or a plurality of the amino acids in that amino acid sequence have been substituted, added or deleted, or an amino acid sequence having homology of 95% or more with that amino acid sequence;

(6) a human antibody κ-type light chain in the form of a monomer in which the variable region is composed of a polypeptide represented by an amino acid sequence consisting of the 1st to 113th amino acids of SEQ ID NO: 38, an amino acid sequence in which one or a plurality of the amino acids in that amino acid sequence have been substituted, added or deleted, or an amino acid sequence having homology of 95% or more with that amino acid sequence;

(7) a human antibody κ-type light chain in the form of a dimer in which the variable region is composed of a polypeptide represented by an amino acid sequence consisting of the 1st to 112th amino acids of SEQ ID NO: 40, an amino acid sequence in which one or a plurality of the amino acids in that amino acid sequence have been substituted, added or deleted, or an amino acid sequence having homology of 95% or more with that amino acid sequence; or (8) a human antibody κ-type light chain in the form of a dimer in which the variable region is composed of a polypeptide represented by an amino acid sequence consisting of the 1st to 107th amino acids of SEQ ID NO: 41, an amino acid sequence in which one or a plurality of the amino acids in that amino acid sequence have been substituted, added or deleted, or an amino acid sequence having homology of 95% or more with that amino acid sequence.

Effects of the Invention

According to the present invention, an anticancer agent can be provided that is highly cytotoxic against cancer cells and particularly lung cancer cells. Since the anticancer agent of the present invention has an antibody enzyme for the active ingredient thereof, it is highly specific for cancer cells. Moreover, since the amino acid sequence of the antibody enzyme is completely human, it is free of problems such as allergies with respect to humans. Consequently, the anticancer agent of the present invention is extremely useful as a highly active, innovative and novel pharmaceutical and as a test piece for the development thereof.

BRIEF DESCRIPTION OF THE DRAWINGS

FIG. 1 is a diagram indicating amino acid sequences of wild type human antibody κ-type light chains. The amino acid sequences appearing in FIG. 1 correspond to the sequence ID numbers assigned in the sequence listing as follows.
1-4(A18b) is SEQ ID NO: 1.
2-3(A3/A19) is SEQ ID NO: 11.
4-1(O2/O1) is SEQ ID NO: 9.
7-2(A3/A19) is SEQ ID NO: 13.
8-2(A18b) is SEQ ID NO: 3.
9a-2(A18b) is SEQ ID NO: 5.
11-1(A18b) is SEQ ID NO: 7.
13-1(A3/A19) is SEQ ID NO: 15.
14-1(A3/A19) is SEQ ID NO: 17.
22F6-4(A3/A19) is SEQ ID NO: 19.
23D4-1(A3/A19) is SEQ ID NO: 21.

FIG. 2A schematically indicates a cDNA design for obtaining a monomer human antibody light chain. The nucleotide sequences appearing in FIG. 2A correspond to the sequence ID numbers assigned in the sequence listing as follows.
The upper nucleotide sequence is SEQ ID NO: 55.
The lower nucleotide sequence is SEQ ID NO: 56.

FIG. 2B schematically indicates the compositions of a human antibody light chain prior to introduction of a mutation and a human antibody light chain following introduction of a mutation.

FIG. 6A is a diagram indicating the amino acid sequences of wild type human antibody κ-type light chains. The amino acid sequences appearing in FIG. 6A correspond to the sequence ID numbers assigned in the sequence listing as follows.
1H31YC220A.pro is SEQ ID NO: 38.
7VL(I).pro is SEQ ID NO: 39.
7RLI.pro is SEQ ID NO: 40.
C51.pro is SEQ ID NO: 41.
C87.pro is SEQ ID NO: 42.

FIG. 6B is a diagram indicating the amino acid sequences of wild type human antibody κ-type light chains.

FIG. 6C is a diagram indicating the amino acid sequences of wild type human antibody κ-type light chains continuing from FIG. 6B.

Figure 3A:
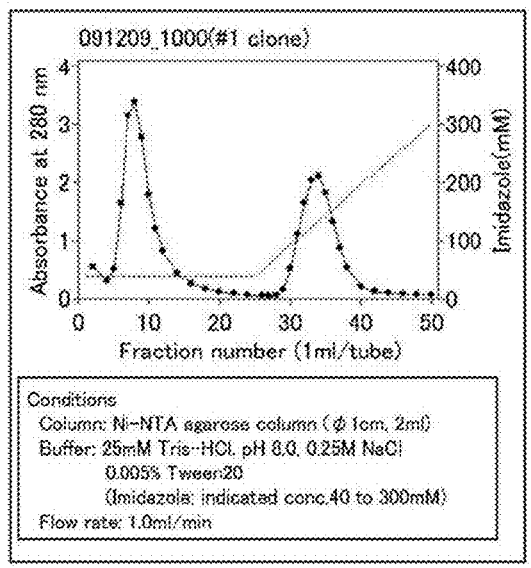
FIG. 3A is a diagram indicating the results of newly carrying out primary purification of a polypeptide of clone #1, and more particularly, is a diagram indicating the results of Ni-NTA column chromatography.

The amino acid sequences appearing in FIG. 6B and FIG. 6C correspond to the sequence ID numbers assigned in the sequence listing as follows.
1H31YC220A.pro is SEQ ID NO: 38.
4.pro is SEQ ID NO: 10.
7EI.pro is SEQ ID NO: 43.
7TR.pro is SEQ ID NO: 44.
7RLI.pro is SEQ ID NO: 40.
7VL.pro is SEQ ID NO: 45.
S13.pro is SEQ ID NO: 46.
S21.pro is SEQ ID NO: 47.
S38.pro is SEQ ID NO: 48.
C51.pro is SEQ ID NO: 41.

FIG. 6D is a diagram indicating the amino acid sequences of wild type human antibody κ-type light chains.

FIG. 6E is a diagram indicating the amino acid sequences of wild type human antibody κ-type light chains continuing from FIG. 6D.

FIG. 6F is a diagram indicating the amino acid sequences of wild type human antibody κ-type light chains continuing from FIG. 6E.

The amino acid sequences appearing in FIG. 6D, FIG. 6E, and FIG. 6F correspond to the sequence ID numbers assigned in the sequence listing as follows.
1H31YC220A.pro is SEQ ID NO: 38.
4.pro is SEQ ID NO: 10.
7.pro is SEQ ID NO: 14.
7RLI.pro is SEQ ID NO: 40.
10.pro is SEQ ID NO: 49.
11.pro is SEQ ID NO: 8.
22F6.pro is SEQ ID NO: 20.
22F6C220A.pro is SEQ ID NO: 54.
C51.pro is SEQ ID NO: 41.
C67.pro is SEQ ID NO: 50.
C82.pro is SEQ ID NO: 51.
C88.pro is SEQ ID NO: 52.

FIG. 6G is a diagram indicating the amino acid sequences of wild type human antibody κ-type light chains.

FIG. 6H is a diagram indicating the amino acid sequences of wild type human antibody κ-type light chains continuing from FIG. 6G.

The amino acid sequences appearing in FIG. 6G and FIG. 6H correspond to the sequence ID numbers assigned in the sequence listing as follows.
4.pro is SEQ ID NO: 10.
7G.pro is SEQ ID NO: 53.
7EI.pro is SEQ ID NO: 43.
7RLI.pro is SEQ ID NO: 40.
7VL.pro is SEQ ID NO: 45.
13.pro is SEQ ID NO: 16.
14.pro is SEQ ID NO: 18.
22F6.pro is SEQ ID NO: 20.

FIG. 6I is a diagram indicating the amino acid sequence of a wild type human antibody κ-type light chain. The amino acid sequence ("#7.pro") appearing in FIG. 6I corresponds to SEQ ID NO: 14 assigned in the sequence listing.

FIG. 7A is a diagram indicating the results of an in vivo assay, and more particularly, indicating the condition of a single-dose oral administration study in animals.

FIG. 7B is a diagram indicating the results of an in vivo assay, and more particularly, indicating the body weight change in animals in the single-dose oral administration study.

FIG. 7C is a diagram indicating the results of an in vivo assay, and more particularly, indicating the macroscopic findings in animals in the single-dose oral administration study.

FIG. 8A is a diagram indicating the results of safety studies (toxicity studies), and more particularly, indicating the toxicity studies conducted in order to confirm the safety to human.

FIG. 8B is a diagram indicating the results of safety studies (toxicity studies), and more particularly, indicating the body weight change in mice in the 7-day repeat-dose toxicity study (caudal vein).

FIG. 8C is a diagram indicating the results of safety studies (toxicity studies), and more particularly, indicating the autopsy findings in mice in the 7-day repeat-dose toxicity study (caudal vein).

BEST MODE FOR CARRYING OUT THE INVENTION

The present invention provides an anticancer agent containing a human antibody κ-type light chain that demonstrates cytotoxicity against cancer cells. In the description of the present application, a "human antibody κ-type light chain" refers to a κ-type light chain of human-derived immunoglobulin.

In the description of the present application, an "anticancer agent" refers to a pharmaceutical agent having an activity that eradicates cancer cells or suppresses or inhibits the proliferation thereof.

In addition, in the description of the present application, "cytotoxicity" refers to a property that induces cell death or causes functional impairment in cells.

More specifically, the active ingredient of the anticancer agent according to the present invention in the form of a human antibody κ-type light chain (to also be referred to as the "human antibody κ-type light chain according to the present invention") is any of those described in (1) to (8) below.

(1) A human antibody κ-type light chain in the form of a dimer in which the variable region is composed of a polypeptide represented by the amino acid sequence of SEQ ID NO: 1, an amino acid sequence in which one or a plurality of the amino acids in that amino acid sequence have been substituted, added or deleted, or an amino acid sequence having homology of 95% or more with that amino acid sequence.

(2) A human antibody κ-type light chain in the form of a dimer in which the variable region is composed of a polypeptide represented by the amino acid sequence of SEQ ID NO: 7, an amino acid sequence in which one or a plurality of the amino acids in that amino acid sequence have been substituted, added or deleted, or an amino acid sequence having homology of 95% or more with that amino acid sequence.

(3) A human antibody κ-type light chain in the form of a dimer in which the variable region is composed of a polypeptide represented by the amino acid sequence of SEQ ID NO: 9, an amino acid sequence in which one or a plurality of the amino acids in that amino acid sequence have been substituted, added or deleted, or an amino acid sequence having homology of 95% or more with that amino acid sequence.

(4) A human antibody κ-type light chain in the form of a dimer in which the variable region is composed of a polypeptide represented by the amino acid sequence of SEQ ID NO: 13, an amino acid sequence in which one or a plurality of the amino acids in that amino acid sequence have been substituted, added or deleted, or an amino acid sequence having homology of 95% or more with that amino acid sequence.

(5) A human antibody κ-type light chain in the form of a monomer in which the variable region is composed of a polypeptide represented by the amino acid sequence of SEQ ID NO: 19, an amino acid sequence in which one or a plurality of the amino acids in that amino acid sequence have been substituted, added or deleted, or an amino acid sequence having homology of 95% or more with that amino acid sequence.

(6) A human antibody κ-type light chain in the form of a monomer in which the variable region is composed of a polypeptide represented by an amino acid sequence consisting of the 1st to 113th amino acids of SEQ ID NO: 38, an amino acid sequence in which one or a plurality of the amino acids in that amino acid sequence have been substituted, added or deleted, or an amino acid sequence having homology of 95% or more with that amino acid sequence.

(7) A human antibody κ-type light chain in the form of a dimer in which the variable region is composed of a polypeptide represented by an amino acid sequence consisting of the 1st to 112th amino acids of SEQ ID NO: 40, an amino acid sequence in which one or a plurality of the amino acids in that amino acid sequence have been substituted, added or deleted, or an amino acid sequence having homology of 95% or more with that amino acid sequence.

(8) A human antibody κ-type light chain in the form of a dimer in which the variable region is composed of a polypeptide represented by an amino acid sequence consisting of the 1st to 107th amino acids of SEQ ID NO: 41, an amino acid sequence in which one or a plurality of the amino acids in that amino acid sequence have been substituted, added or deleted, or an amino acid sequence having homology of 95% or more with that amino acid sequence.

The human antibody κ-type light chain in the form of a dimer in which the variable region is composed of a polypeptide represented by the amino acid sequence of SEQ ID NO: 1 may also be referred to as human antibody κ-type light chain (#1). The human antibody κ-type light chain (#1) can have a known human antibody constant region added to the aforementioned variable region, and in one embodiment, the entire length of the amino acid sequence is as shown in SEQ ID NO: 2. CDR1 in the human antibody κ-type light chain (#1) consists of the 24th to 39th amino acids in the amino acid sequences of SEQ ID NO: 1 and SEQ ID NO: 2, CDR2 consists of the 55th to 61st amino acids in the amino acid sequences of SEQ ID NO: 1 and SEQ ID NO: 2, and CDR3 consists of the 94th to 102nd amino acids in the amino acid sequences of SEQ ID NO: 1 and SEQ ID NO: 2.

A cysteine residue for forming a disulfide bond is present in a wild type antibody κ-type light chain that results in the formation of a dimer. The human antibody κ-type light chain (#1) also has a cysteine residue for forming a disulfide bond with another light chain in the same manner as the wild type. For example, in the case the human antibody κ-type light chain (#1) is composed of a polypeptide represented by the amino acid sequence of SEQ ID NO: 2, then the cysteine residue is the cysteine residue at position 220 in the amino acid sequence of SEQ ID NO: 2.

As will be subsequently indicated in the examples, the human antibody κ-type light chain (#1) demonstrates cytotoxicity against cancer cells and particularly lung cancer cells. Consequently, it is preferable for use as an active ingredient of an anticancer agent. Since the ability to accurately recognize a target molecule is important for the human antibody κ-type light chain (#1) to demonstrate anticancer activity, the active center of the anticancer activity of the human antibody κ-type light chain (#1) is in the variable region.

Being able to easily modify several amino acids among amino acid residues composing a polypeptide without having a significant effect on the structure or function of the polypeptide is commonly known in the art. Moreover, in addition to artificial modification, mutants are also commonly known to exist in naturally-occurring proteins that do not cause a significant change in the structure or function of that protein. Furthermore, in the description of the present application, the substitution, addition or deletion of one or a plurality of amino acids in a specific amino acid sequence X is referred to as mutation.

The human antibody κ-type light chain according to the present invention may form a dimer in which the variable region is composed of a polypeptide represented by an amino acid sequence in which one or a plurality of amino acids in the amino acid sequence of SEQ ID NO: 1 have been substituted, added or deleted, or an amino acid sequence having homology of 95% or more with that amino acid sequence. This polypeptide may also be referred to as a mutant of the human antibody κ-type light chain (#1). A mutant of the human antibody κ-type light chain (#1) may also be composed of a polypeptide represented by an amino acid sequence in which one or a plurality of amino acids other than the cysteine at position 220 in the amino acid sequence of SEQ ID NO: 2 have been substituted, added or deleted, or an amino acid sequence having homology of 95% or more with that amino acid sequence.

A mutant of the human antibody κ-type light chain (#1) used as the human antibody κ-type light chain according to the present invention is a dimer having an anticancer action in the same manner as the human antibody κ-type light chain (#1). Consequently, CDR1, CDR2 and CDR3 of a mutant of the human antibody κ-type light chain (#1) are identical to the amino acid sequence of SEQ ID NO:1 or SEQ ID NO: 2 (are preserved therein), and the cysteine corresponding to cysteine at position 220 in the amino acid sequence of SEQ ID NO: 2 is also preserved. In other words, a mutant of the human antibody κ-type light chain (#1) is preferably such that amino acids in regions other than CDR1, CDR2 and CDR3 are mutated and amino acids in other regions of the variable region are mutated.

A human antibody κ-type light chain in the form of a dimer in which the variable region is composed of a polypeptide represented by the amino acid sequence of SEQ ID NO: 9 may also be referred to as human antibody κ-type light chain (#4). The human antibody κ-type light chain (#4) can have a known human antibody constant region added to the aforementioned variable region, and in one embodiment, the entire length of the amino acid sequence is as shown in SEQ ID NO: 10. CDR1 in the human antibody κ-type light chain (#4) consists of the 24th to 40th amino acids in the amino acid sequences of SEQ ID NO: 9 and SEQ ID NO: 10, CDR2 consists of the 56th to 62nd amino acids in the amino acid sequences of SEQ ID NO: 9 and SEQ ID NO: 10, and CDR3 consists of the 95th to 102nd amino acids in the amino acid sequences of SEQ ID NO: 9 and SEQ ID NO: 10. In addition, a cysteine residue for forming a disulfide bond with another light chain is the cysteine residue at position 220 in the amino acid sequence of SEQ ID NO: 10.

As will be subsequently indicated in the examples, the human antibody κ-type light chain (#4) demonstrates cytotoxicity against cancer cells and particularly lung cancer cells. Consequently, it is preferable for use as an active ingredient of an anticancer agent.

The human antibody κ-type light chain according to the present invention may form a dimer in which the variable region is composed of a polypeptide represented by an amino acid sequence in which one or a plurality of amino acids in the amino acid sequence of SEQ ID NO: 9 have been substituted, added or deleted, or an amino acid sequence having homology of 95% or more with that amino acid sequence. This polypeptide may also be referred to as a mutant of the human antibody κ-type light chain (#4). A mutant of the human antibody κ-type light chain (#4) may also be composed of a polypeptide represented by an amino acid sequence in which one or a plurality of amino acids other than the cysteine at position 220 in the amino acid sequence of SEQ ID NO: 10 have been substituted, added or deleted, or an amino acid sequence having homology of 95% or more with that amino acid sequence.

A mutant of the human antibody κ-type light chain (#4) used as the human antibody κ-type light chain according to the present invention is a dimer having an anticancer action in the same manner as the human antibody κ-type light chain (#4). Consequently, CDR1, CDR2 and CDR3 of a mutant of the human antibody κ-type light chain (#4) are identical to the amino acid sequence of SEQ ID NO:9 or SEQ ID NO: 10 (are preserved therein), and the cysteine corresponding to cysteine at position 220 in the amino acid sequence of SEQ ID NO: 10 is also preserved. In other words, a mutant of the human antibody κ-type light chain (#4) is preferably such that amino acids in regions other than CDR1, CDR2 and CDR3 are mutated and amino acids in other regions of the variable region are mutated.

A human antibody κ-type light chain in the form of a dimer in which the variable region is composed of a polypeptide represented by the amino acid sequence of SEQ ID NO: 13 may also be referred to as human antibody κ-type light chain (#7). The human antibody κ-type light chain (#7) can have a known human antibody constant region added to the aforementioned variable region, and in one embodiment, the entire length of the amino acid sequence is as shown in SEQ ID NO: 14. CDR1 in the human antibody κ-type light chain (#7) consists of the 24th to 39th amino acids in the amino acid sequences of SEQ ID NO: 13 and SEQ ID NO: 14, CDR2 consists of the 55th to 61st amino acids in the amino acid sequences of SEQ ID NO: 13 and SEQ ID NO: 14, and CDR3 consists of the 94th to 101st amino acids in the amino acid sequences of SEQ ID NO: 13 and SEQ ID NO: 14. In addition, a cysteine residue for forming a disulfide bond with another light chain is the cysteine residue at position 219 in the amino acid sequence of SEQ ID NO: 14.

As will be subsequently indicated in the examples, the human antibody κ-type light chain (#7) demonstrates cytotoxicity against cancer cells and particularly lung cancer cells. Consequently, it is preferable for use as an active ingredient of an anticancer agent.

The human antibody κ-type light chain according to the present invention may form a dimer in which the variable region is composed of a polypeptide represented by an amino acid sequence in which one or a plurality of amino acids in the amino acid sequence of SEQ ID NO: 13 have been substituted, added or deleted, or an amino acid sequence having homology of 95% or more with that amino acid sequence. This polypeptide may also be referred to as a mutant of the human antibody κ-type light chain (#7). A mutant of the human antibody κ-type light chain (#7) may also be composed of a polypeptide represented by an amino acid sequence in which one or a plurality of amino acids other than the cysteine at position 219 in the amino acid sequence of SEQ ID NO: 14 have been substituted, added or deleted, or an amino acid sequence having homology of 95% or more with that amino acid sequence.

A mutant of the human antibody κ-type light chain (#7) used as the human antibody κ-type light chain according to the present invention is a dimer having an anticancer action in the same manner as the human antibody κ-type light chain (#7). Consequently, CDR1, CDR2 and CDR3 of a mutant of the human antibody κ-type light chain (#7) are identical to the amino acid sequence of SEQ ID NO:13 or SEQ ID NO: 14 (are preserved therein), and the cysteine corresponding to cysteine at position 219 in the amino acid sequence of SEQ ID NO: 14 is also preserved. In other words, a mutant of the human antibody κ-type light chain (#7) is preferably such that amino acids in regions other than CDR1, CDR2 and CDR3 are mutated and amino acids in other regions of the variable region are mutated.

A human antibody κ-type light chain in the form of a monomer in which the variable region is composed of a polypeptide represented by the amino acid sequence of SEQ ID NO: 19 may also be referred to as human antibody κ-type light chain (22F6_monomer). The human antibody κ-type light chain (22F6_monomer) can have a known human antibody constant region added to the aforementioned variable region, and in one embodiment, the entire length of the amino acid sequence is represented by an amino acid sequence in which the 219th cysteine in the amino acid sequence of SEQ ID NO: 20 has been deleted or substituted with another amino acid (such as alanine). CDR1 in the human antibody κ-type light chain (22F6_monomer) consists of the 24th to 39th amino acids in the amino acid sequences of SEQ ID NO: 19 and SEQ ID NO: 20, CDR2 consists of the 55th to 61st amino acids in the amino acid sequences of SEQ ID NO: 19 and SEQ ID NO: 20, and CDR3 consists of the 94th to 101st amino acids in the amino acid sequences of SEQ ID NO: 19 and SEQ ID NO: 20.

As will be subsequently indicated in the examples, the human antibody κ-type light chain (22F6_monomer) demonstrates cytotoxicity against cancer cells and particularly lung cancer cells. Consequently, it is preferable for use as an active ingredient of an anticancer agent.

The human antibody κ-type light chain according to the present invention may be a monomer in which the variable region is composed of a polypeptide represented by an amino acid sequence in which one or a plurality of amino acids in the amino acid sequence of SEQ ID NO: 20 have been substituted, added or deleted, or an amino acid sequence having homology of 95% or more with that amino acid sequence. This polypeptide may also be referred to as a mutant of the human antibody κ-type light chain (22F6_monomer). A mutant of the human antibody κ-type light chain (22F6_monomer) may also be composed of a polypeptide represented by an amino acid sequence in which the 219th cysteine has been deleted or substituted with another amino acid and one or a plurality of amino acids other than the amino acid at position 219 have been substituted, added or deleted in the amino acid sequence of SEQ ID NO: 20, or an amino acid sequence having homology of 95% or more with that amino acid sequence.

A mutant of the human antibody κ-type light chain (22F6_monomer) used as the human antibody κ-type light chain according to the present invention is a monomer having an anticancer action in the same manner as the human antibody κ-type light chain (22F6_monomer). Consequently, CDR1, CDR2 and CDR3 of a mutant of the human antibody κ-type light chain (22F6_monomer) are identical to the amino acid sequence of SEQ ID NO: 19 or SEQ ID NO: 20 (are preserved therein), and the cysteine corresponding to cysteine at position 219 in the amino acid sequence of SEQ ID NO: 20 is deleted or substituted with another amino acid. In other words, a mutant of the human antibody κ-type light chain (22F6_monomer) is preferably such that amino acids in regions other than CDR1, CDR2 and CDR3 are mutated and amino acids in other regions of the variable region are mutated.

In addition, the human antibody κ-type light chain according to the present invention may also contain an additional polypeptide. Typical examples of additional polypeptides include epitope-tagged polypeptides such as those tagged with His tag, Myc or Flag.

A person with ordinary skill in the art is able to easily mutate one or a plurality of amino acids among amino acid residues that compose a polypeptide or add an epitope-tagged polypeptide using a known technology. For example, an arbitrary base of a polynucleotide that encodes a polypeptide can be mutated in accordance with a known point mutagenesis method. In addition, a primer corresponding to an arbitrary site of a polynucleotide that encodes a polypeptide can be designed to create a deletion mutant or an addition mutant.

The human antibody κ-type light chain according to the present invention includes a naturally-occurring purification product, a product obtained by a chemical synthesis procedure, and a product produced by recombination technology from a prokaryotic host or eukaryotic host (including bacterial cells, yeast cells, higher plant cells, insect cells and mammalian cells). The human antibody κ-type light chain may or may not be glycosylated depending on the host used in the recombinant production procedure. Moreover, the human antibody κ-type light chain according to the present invention can contain a modified initiating methionine group in several cases as a result of a host intervention process.

Although the human antibody κ-type light chain according to the present invention may be a polypeptide in which amino acids are linked by peptide bonds, it is not limited thereto, and the polypeptide may also be a composite polypeptide containing a structure other than that of a polypeptide. As used in the present description, although examples of a "structure other than that of a polypeptide" include sugar chains and isoprenoid groups, there are no particular limitations thereon.

The human antibody κ-type light chain according to the present invention can be produced using an expression system known in the art, such as a recombination expression system or a cell-free expression system, by using a vector containing a polynucleotide encoding the human antibody κ-type light chain (polypeptide).

In the case of using a recombination expression system, a method can be employed having the steps of, for example, incorporating a polynucleotide encoding the human antibody κ-type light chain according to the present invention into a recombination expression vector followed by introducing into a host enabling expression thereof according to a known method, translating within the host (transformant) and purifying the resulting polypeptide. The recombination expression vector may or may not be a plasmid, and is only required to enable the target polynucleotide to be introduced into the host.

In the case of introducing an exogenous polynucleotide into a host in this manner, a promoter that functions in the host so as to express exogenous polynucleotides is preferably incorporated into the expression vector. Although the method used to purify the recombinantly produced polypeptide varies according to the properties of the host and polypeptide used, a target polypeptide can be purified comparatively easily using a tag and the like.

In the case of using a cell-free expression system (cell-free protein synthesis system), a polynucleotide encoding the human antibody κ-type light chain according to the present invention is preferably added to a solution containing components such as ribosomes or t-RNA required for protein translation and synthesis followed by incubating at a suitable temperature and purifying the synthesized polypeptide.

Examples of cell-free protein synthesis systems include systems using wheat germ extract, systems using rabbit reticulocyte extract, systems using E. coli S30 extract and systems using cell component extracts obtained from plant devacuolated protoplasts. In general, although eukaryotic cell systems, namely, systems using wheat germ extract or systems using rabbit reticulocyte extract, are selected for translation of eukaryotic genes, the aforementioned synthesis system is selected in consideration of such factors as the origin of the gene to be translated (prokaryotic or eukaryotic) or the purpose for which the protein is to be used following synthesis. Various commercially available kits can be used for these synthesis systems.

Furthermore, since various viral gene products frequently express activity by going through a complex biochemical reaction involving the cytomembrane, such as the endoplasmic reticulum or Golgi bodies, following translation, it is necessary to add cytomembrane components (such as microsomal membrane) in order to reproduce the various biochemical reactions in vitro. Cell component extracts obtained from plant devacuolated protoplasts are preferable since they can be used as a cell-free protein synthesis liquid that retains cytomembrane components, thereby eliminating the need to add microsomal membrane.

As used in the present description, "cytomembrane components" are intended to refer to cell organelles composed of lipid membrane present in the cytomembrane (namely, all types of intracellular granules such as endoplasmic reticulum, Golgi bodies, mitochondria, chloroplast and vacuoles). In particular, since endoplasmic reticulum and Golgi bodies fulfill an important role in post-translation modification of proteins, they are essential cell components for maturation of membrane proteins and secretory proteins.

Human antibody κ-type light chain synthesized with a host expression system or a cell-free protein synthesis system is preferably purified. Although a step for purifying human antibody κ-type light chain is preferably a step in which a cell extract is prepared from cells or tissue using a known method (such as a method in which the cells or tissue is homogenized, followed by centrifuging and recovering the soluble fraction), followed by purifying the human antibody κ-type light chain from this cell extract using a known method (such as ammonium sulfate precipitation or ethanol precipitation, acid extraction, anionic or cationic chromatography, phosphocellulose chromatography, hydrophobic interaction chromatography, affinity chromatography, hydroxyapatite chromatography or lectin chromatography), it is not limited thereto. High-performance liquid chromatography (HPLC) is most preferably used for purification.

In addition, the human antibody κ-type light chain according to the present invention can also be purified from cells or tissues that express the human antibody κ-type light chain in nature. For example, cells or tissues that express the human antibody κ-type light chain according to the present invention in nature can be identified using an antibody or an oligonucleotide. Purification of a human antibody κ-type light chain from cells or tissue can also be carried out in the same manner as in the case of purifying a human antibody κ-type light chain synthesized using a host expression system and the like.

In addition, the human antibody κ-type light chain according to the present invention can also be chemically synthesized. There are no particular limitations on the chemical synthesis method, and may be carried out by any method used when chemically synthesizing polypeptides.

The anticancer agent according to the present invention has the human antibody κ-type light chain according to the present invention as an active ingredient thereof. Although the mechanism of action by which the human antibody κ-type light chain according to the present invention demonstrates cytotoxicity against cancer cells has not been completely determined, it is presumed that, as a result of the human antibody κ-type light chain according to the present invention specifically recognizing and binding to a specific molecule or structure on the surface of cancer cells simultaneous to decomposing a portion of the components of cancer cells by utilizing its own enzyme activity, the function of the cancer cells is impaired, proliferation thereof is inhibited or cell death is induced.

The anticancer agent according to the present invention can be injected or administered directly for use in humans or animals. The anticancer agent according to the present invention can also be formulated for parenteral administration, mucosal administration, intramuscular administration, intravenous administration, subcutaneous administration, intraocular administration or transcutaneous administration. Typically, protein contained in a composition can be administered at a dose of 0.01 mg/kg to 30 mg/kg of body weight, preferably at 0.1 mg/kg to 10 mg/kg of body weight, and even more preferably at 0.1 mg/kg to 1 mg/kg of body weight.

The anticancer agent according to the present invention can also contain a pharmaceutically acceptable carrier, diluent or vehicle (including combinations thereof) in addition to the human antibody κ-type light chain according to the present invention. Pharmaceutically acceptable carriers or vehicles for therapeutic use are commonly known in the field of pharmacy, and are described in, for example, Remington's Pharmaceutical Sciences, Mack Publishing Co. (A. R. Gennaro, ed., 1985). Pharmaceutically usable carriers, vehicles or diluents can be suitably selected by a person with ordinary skill in the art in accordance with the intended administration route and standard pharmaceutical practices. In addition, the anticancer agent according to the present invention can further contain an arbitrary suitable binder, lubricant, suspension agent, coating agent or solubilizing agent.

Conditions required for composition and/or formulation can vary depending on the use of different delivery systems. As an example thereof, the anticancer agent according to the present invention can be formulated so as to be delivered using a minipump, by a mucosal route in the form of, for example, a nasal spray or aerosol for inhalation, or for parenteral delivery (here, the anticancer agent according to the present invention is formulated in an injectable form for delivery via, for example, an intravenous route, an intramuscular route or a subcutaneous route). Alternatively, the formula can be designed so as to be delivered by both routes. For example, the anticancer agent according to the present invention demonstrates a high level of cytotoxicity against lung cancer cells in particular. Consequently, the anticancer agent according to the present invention is preferably in the form of a nasal spray or aerosol for inhalation that enables it to be efficiently delivered to pneumocytes from the nose or bronchi.

In addition, in the case of using the anticancer agent according to the present invention in an application in which it is administered into the body, various technologies can be used for improving the stability (half-life in blood) of the active ingredient in the form of the human antibody κ-type light chain in the body. For example, the half-life in the blood of antibodies such as IgG is known to be prolonged if neonatal Fc receptor (FcRn) is bound to the Fc region (see, for example, Roopenian, D. C., et al., Nat. Rev. Immunol., Vol. 7, 715-725 (2007)), and the C-terminal of the human antibody κ-type light chain according to the present invention can be modified so as to have binding activity with FcRn. In addition, the human antibody κ-type light chain according to the present invention can be in the form of a dimer, and polyethylene glycol (PEG) can be added as well.

The anticancer agent according to the present invention can be incorporated in a kit, for example, together with instructions and the like on the form in which it is to be administered. The kit can also contain various other pharmaceuticals that can be used with the anticancer agent according to the present invention.

In addition, since the anticancer agent according to the present invention has for the active ingredient thereof an antibody κ-type light chain that is highly effective in recognizing a target molecule, it does not demonstrate cytotoxicity against cancer cells in which the target molecule of the antibody light chain is not present on the cell surface thereof. Consequently, the anticancer agent of the present invention is expected to be useful in distinguishing types of cancer.

EXAMPLES

Although the following provides a more detailed explanation of the present invention through examples thereof, the present invention is not limited by these examples.

Example 1

(1. Preparation of Human Peripheral Blood cDNA)

Lymphocytes were isolated using Ficoll-paque from peripheral blood acquired from volunteers hyperimmunized over a plurality of times using rabies virus vaccine. Total RNA was obtained from roughly $3.0 \times 10^7$ isolated lymphocytes using an RNA extraction kit (Stratagene Corp.). The target cDNA (cDNA library) was then prepared by reverse transcribing the total RNA with the ThermoScript RT-PCT System (Invitrogen Inc.) using oligo(dT) as primer.

(2. Acquisition of Human Antibody κ-Type Light Chain Genes)

PCR reactions were carried out in two stages using the cDNA acquired in step 1 above as template and using primers for amplifying antibody light chain gene having a Vκ gene belonging to subgroup II to obtain roughly 750 bp PCR products (κ-type light chain genes belonging to subgroup II). These PCR products were cloned and subjected to sequence analysis, and the Vκ gene in each germline gene was estimated by a homology search. As a result, all of the resulting 18 clones belonged to subgroup II. Among these, nine clones, namely, clone #1 (germline genotype: A18b), clone #2 (germline genotype: A3/A19), clone #4 (germline genotype: 011/ol), clone #7 (germline genotype: A3/A19), clone #8 (germline genotype: A18b), clone #9 (germline genotype: A18b), clone #11 (germline genotype: A18b), clone #13 (germline genotype: A3/A19) and clone #14 (germline genotype: A3/A19) were used in subsequent experimentation.

(3. Expression of Human Antibody κ-Type Light Chains)

Each of the clones acquired in step 2 above was respectively introduced into a plasmid vector having an His tag sequence site followed by introducing the plasmid vector into *Escherichia coli* to produce transformants. When each transformant was cultured and subjected to induction of expression with IPTG, the protein expressed in the *E. coli* was able to be identified as a human antibody light chain by SDS-PAGE analysis and Western blotting using anti-human (Fab')$_2$ antibody. The resulting human antibody light chains had M (initiating methionine) on the N-terminal and LEHHHHHH (SEQ ID NO: 23) derived from the plasmid vector on the C-terminal.

(4. Preparation of Human Peripheral Blood cDNA)

Subjects were hyperimmunized over a plurality of times using rabies virus vaccine followed by measurement of serum neutralizing activity. Peripheral blood was collected from the donor subject having the highest level of serum neutralizing activity (7.21 U), and lymphocytes were isolated from the peripheral blood using Ficoll-paque. Total RNA was then obtained from roughly $3.0 \times 10^7$ isolated lymphocytes using an RNA extraction kit (Stratagene Corp.). cDNA to be used as template was prepared in a PCR reaction to be subsequently described by reverse transcribing the total RNA with the ThermoScript RT-PCR System (Invitrogen Inc.) using oligo(dT) as primer.

(5. Acquisition of Human Antibody κ-Type Light Chain Genes)

A PCR reaction was carried out using a primer set for comprehensively amplifying human antibody light chain gene and using the cDNA acquired in step 4 above as template to obtain a roughly 660 bp PCR product. This PCR product was purified and inserted into the *E. coli* expression vector pET101/D-TOPO® (Invitrogen Inc.) to construct an LCA library. Furthermore, protein in which an His tag was added to the C-terminal of the protein encoded by the PCR product was expressed from an expression vector in which the PCR product was inserted in the pET101/D-TOPO vector. PCR reactions were carried out using the cDNA of this LCA library as template and using primers for amplifying human antibody light chain gene having a Vκ gene belonging to subgroup II to obtain roughly 660 bp PCR products. These PCR products were cloned and subjected to sequence analysis and their amino acid sequences and light chain variable and constant regions were estimated using analytical software (Genetix® Ver. 8) followed by estimation of the Vκ gene in each germline gene. Among these clones, two clones, namely, clone 22F6 (germline genotype: A3/A19) and clone 23D4 (germline genotype: A3/A19) were used in subsequent experimentation. The resulting human antibody light chains had M (initiating methionine) on the N-terminal and LEHHHHHH (SEQ ID NO: 23) derived from the plasmid vector on the C-terminal.

As a result of sequencing each clone, the total length of the human antibody light chain pertaining to clone #1 (human antibody light chain (#1_WT)) was the base sequence indicated in SEQ ID NO: 27, the total length of the human antibody light chain pertaining to clone #8 (human antibody light chain (#8_WT)) was the base sequence indicated in SEQ ID NO: 28, the total length of the human antibody light chain pertaining to clone #9 (human antibody light chain (#9_WT)) was the base sequence indicated in SEQ ID NO: 29, the total length of the human antibody light chain pertaining to clone #11 (human antibody light chain (#11_WT)) was the base sequence indicated in SEQ ID NO: 30, the total length of the human antibody light chain pertaining to clone #4 (human antibody light chain (#4_WT)) was the base sequence indicated in SEQ ID NO: 31, the total length of the human antibody light chain pertaining to clone #2 (human antibody light chain (#2 WT)) was the base sequence indicated in SEQ ID NO: 32, the total length of the human antibody light chain pertaining to clone #7 (human antibody light chain (#7_WT)) was the base sequence indicated in SEQ ID NO: 33, the total length of the human antibody light chain pertaining to clone #13 (human antibody light chain (#13_WT)) was the base sequence indicated in SEQ ID NO: 34, the total length of the human antibody light chain pertaining to clone #14 (human antibody light chain (#14_WT)) was the base sequence indicated in SEQ ID NO: 35, the total length of the human antibody light chain pertaining to clone 22F6 (human antibody light chain (22F6_WT)) was the base sequence indicated in SEQ ID NO: 36, and the total length of the human antibody light chain pertaining to clone 23D4 (human antibody light chain (23D4 WT)) was the base sequence indicated in SEQ ID NO: 37.

The amino acid sequences estimated from each of the base sequences are shown in FIG. 1. In addition, the locations of the variable regions, constant regions and CDR1 to CDR3 are also shown. The human antibody light chain pertaining to clone #1 (human antibody light chain (#1_WT)) was the amino acid sequence shown in SEQ ID NO: 2, the human antibody light chain pertaining to clone #8 (human antibody light chain (#8_WT)) was the amino acid sequence shown in SEQ ID NO: 4, the human antibody light chain pertaining to clone #9 (human antibody light chain (#9_WT)) was the amino acid sequence shown in SEQ ID NO: 6, the human antibody light chain pertaining to clone #11 (human antibody light chain (#11_WT)) was the amino acid sequence shown in SEQ ID NO: 8, the human antibody light chain pertaining to clone #4 (human antibody light chain (#4_WT)) was the amino acid sequence shown in SEQ ID NO: 10, the human antibody light chain pertaining to clone #2 (human antibody light chain (#2_WT)) was the amino acid sequence shown in SEQ ID NO: 12, the human antibody light chain pertaining to clone #7 (human antibody light chain (#7_WT)) was the amino acid sequence shown in SEQ ID NO: 14, the human antibody light chain pertaining to clone #13 (human antibody light chain (#13_WT)) was the amino acid sequence shown in SEQ ID NO: 16, the human antibody light chain pertaining to clone #14 (human antibody light chain (#14_WT)) was the amino acid sequence shown in SEQ ID NO: 18, the human antibody light chain pertaining to clone 22F6 (human antibody light chain (22F6_WT)) was the amino acid sequence shown in SEQ ID NO: 20, and the human antibody light chain pertaining to clone 23D4 (human antibody light chain (23D4_WT)) was the amino acid sequence shown in SEQ ID NO: 22.

Furthermore, the wild type human antibody light chains used in the present example were polypeptides in which methionine was added to the N-terminal of each amino acid sequence shown in FIG. 1 and LEHHHHH (SEQ ID NO: 23) derived from the plasmid vector was added to the C-terminal.

(6. Production of Monomer Human Antibody Light Chains)

The human antibody κ-type light chains of the clones acquired in steps 2 and 5 above formed dimers due to the formation of disulfide (S—S) bonds by cysteine on the C-terminal. Then, cDNA was designed so as to form only monomer human antibody enzymes by introducing a mutation in which the cysteine involved in S—S bond formation (cysteine on the C-terminal of the amino acid sequences of FIG. 1) is substituted with alanine. The details of this design with respect to the human antibody light chain having LEHHHHHH derived from the plasmid vector on the C-terminal thereof (#1_WT) are shown in FIGS. 2A and 2B. As shown in FIG. 2A, TGT encoding cysteine at position 220 in the full-length human antibody enzyme gene is substituted with GCT. As a result, as shown in FIG. 2B, although a dimer is formed in the original amino acid sequence due to the presence of cysteine at position 220, S—S bonds are not formed in the substituted amino acid sequence as a result of substituting alanine at position 220, thereby resulting in a monomer.

More specifically, TGT encoding the aforementioned cysteine in the wild-type full-length human antibody enzyme gene was substituted with GCTCTCGAGCACCACCAC-CACCACCACTGA (SEQ ID NO: 26) that encodes ALE- HHHHHH (SEQ ID NO: 25) (having a stop codon). In other words, the monomer human antibody light chain used in the present example was a polypeptide in which methionine was added to the N-terminal of each amino acid sequence shown in FIG. 1 and ALEHHHHHH was added to the C-terminal instead of cysteine. Furthermore, among those mutants obtained in this manner, in which the cysteine involved in S—S bonding was substituted with alanine, the mutant of human antibody light chain (#1_WT) is referred to as the human antibody light chain(#1_C220A), the mutant of human antibody light chain (#8_WT) is referred to as the human antibody light chain(#8_C220A), the mutant of human antibody light chain (#9_WT) is referred to as the human antibody light chain(#9_C220A), the mutant of human antibody light chain (#11_WT) is referred to as the human antibody light chain(#11_C220A), the mutant of human antibody light chain (#4_WT) is referred to as the human antibody light chain(#4_C220A), the mutant of human antibody light chain (#2_WT) is referred to as the human antibody light chain(#2_C220A), the mutant of human antibody light chain (#7_WT) is referred to as the human antibody light chain(#7_C220A), the mutant of human antibody light chain (#13_WT) is referred to as the human antibody light chain(#13_C220A), the mutant of human antibody light chain (#14_WT) is referred to as the human antibody light chain(#14_C220A), the mutant of human antibody light chain (22F6_WT) is referred to as the human antibody light chain(22F6_C220A) and the mutant of human antibody light chain (23D4_WT) is referred to as the human antibody light chain(23D4_C220A).

(7. Purification of Human Antibody Light Chains)

Figure 3B:
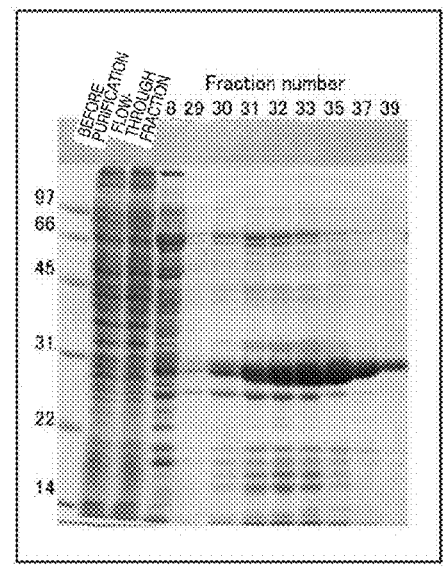
FIG. 3B is a diagram indicating the results of newly carrying out primary purification of a polypeptide of clone #1, and more particularly, is a stained image of SDS-PAGE analysis.
Figure 3C:
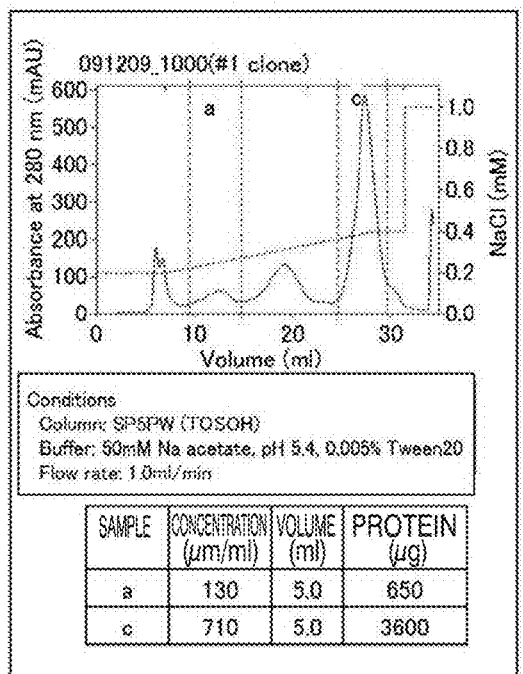
FIG. 3C is a diagram indicating the results of newly carrying out secondary purification of the polypeptide of clone #1, and more particularly, is a diagram indicating the results of cation exchange chromatography.
Figure 3D:
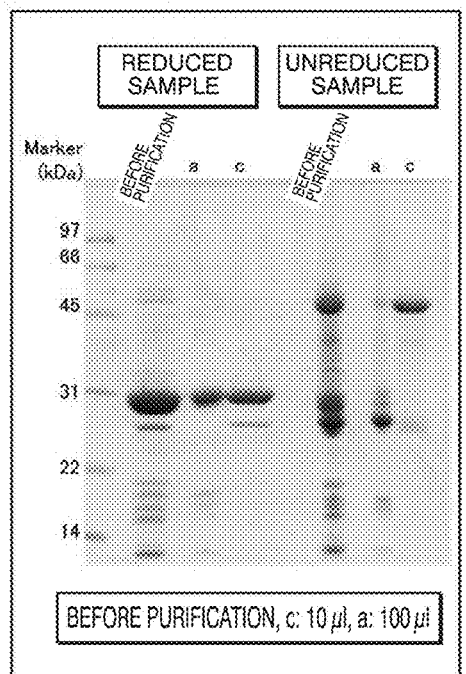
FIG. 3D is a diagram indicating the results of newly carrying out secondary purification of the polypeptide of clone #1, and more particularly, is a stained image of SDS-PAGE analysis.

Each of the human antibody light chains was subjected to primary purification and secondary purification in the manner described below. FIG. 3A is a diagram indicating the results of Ni-NTA column chromatography and FIG. 3B is a stained image of SDS-PAGE analysis during primary purification of human antibody light chain (#1_WT) and human antibody light chain (#1_C220A). FIG. 3C is a diagram indicating the results of cation exchange chromatography and FIG. 3D is a stained image of SDS-PAGE analysis during secondary purification.

As shown in FIG. 3A, buffer A (25 mM Tris-HCl (pH 8.0), 0.25 M NaCl, 40 mM imidazole and 0.005% Tween 20) was passed through the column after applying the sample until all the flow-through fraction had passed through the column. As indicated by the broken line in the graph on the left side, the concentration of imidazole was increased gradually from 40 mM to 300 mM to elute a component bound to the gel. An Ni-NTA agarose column (diameter: 1 cm, 2 ml) was used for the column and the flow rate was maintained at 0.1 mL/min throughout purification. As shown in FIG. 3B, a target band of roughly 31 kDa was detected in fractions 30 to 37. These samples were combined and subjected to the secondary purification indicated below.

As shown in FIG. 3C, buffer A (50 mM sodium acetate (pH 5.4), 0.2 M NaCl and 0.005% Tween 20) was passed through the column after applying the sample until all the flow-through fraction had passed through the column. As indicated by the broken line in the graph on the left side, the concentration of NaCl was increased gradually from 0.2 M to 0.4 M to elute a component bound to the gel. The SP5PW column (Tosho Corp.) was used for the column and the flow rate was maintained at 0.1 ml/min throughout purification. Components contained in the sample prior to purification, the region "a" surrounded by broken lines in the graph (fraction numbers 10 to 15) and the region "c" surrounded by broken lines in the graph (fraction numbers 25 to 30) were analyzed by SDS-PAGE. As shown in FIG. 3D, a target band of roughly 31 kDa was detected in regions "a" and "c" in the reduced sample. In addition, in the unreduced sample, a roughly 31 kDa band was detected only in region "a" while a roughly 51 kDa band was detected only in region "c". As has been described above, the monomer of the antibody light chain is roughly 31 kDa and the dimer is roughly 51 kDa. Sample a is the monomer fraction of the antibody light chain while sample c is the dimer fraction of the antibody light chain.

The other clones also contained dimers and monomers in the expression products of the wild-type human antibody light chains in the same manner as clone (#1), dimers were purified by two-stage purification utilizing Ni-NTA column chromatography and cation exchange chromatography, monomers were contained in the expression products of mutants in which cysteine involved in S—S bonding had been mutated to alanine, and the monomers were purified by the same two-stage purification.

(8. Cytotoxicity Against Cancer Cells)

A test was conducted of the cytotoxicity of various human antibody κ-type light chains against cancer cells. Human alveolar adenocarcinoma cell line A549 purchased from ATCC was used for the cancer cells, and the cells were cultured in accordance with routine methods using F-12K medium containing 10% fetal calf serum (FCS).

First, after thawing and recovering frozen A549 cells, 100 µl aliquots of the cells were disseminated in a 96-well plate to a concentration of $5 \times 10^3$ cells/well. After culturing for 24 hours at 37° C. and removing the medium added to the 96-well plate by decantation, each human antibody κ-type light chain adjusted to a concentration of about 1 mg/mL was added in 100 µL aliquots to each well. 10 µl aliquots of WST-1 reagent (Roche Diagnostics GmbH) were added to each well at 24 hours and 48 hours after adding the human antibody κ-type light chains (48 hours and 72 hours after disseminating the cells), followed by measurement of absorbance of the formasan pigment formed (Abs 450 nm) 1, 1.5 and 2 hours later. Cell viability was determined in each well based on the resulting absorbance results using a value of 100% for cell viability in a well to which a human antibody κ-type light chain was not added (N.C.) followed by evaluation of cytotoxicity of the added human antibody κ-type light chains.

Figure 4:
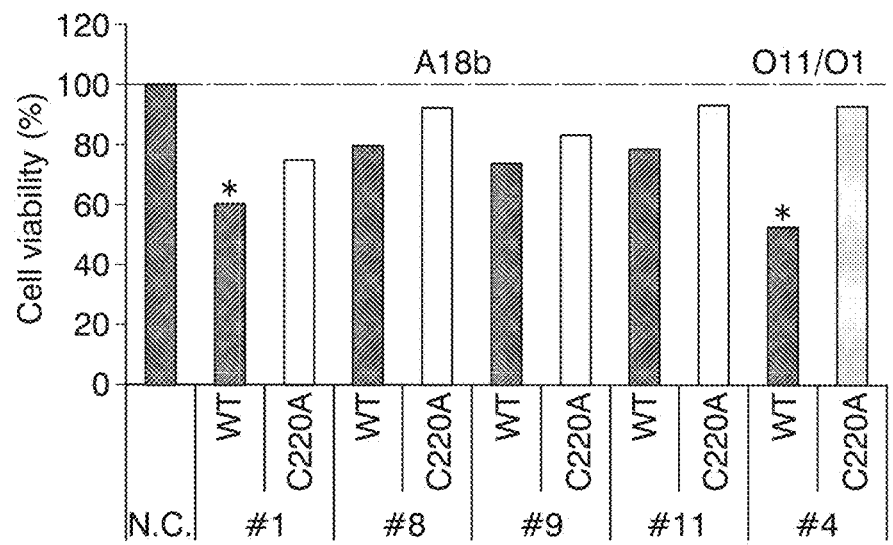
FIG. 4 is a graph indicating the results of investigating the cytotoxicity of various clones against cancer cells.
Figure 5:
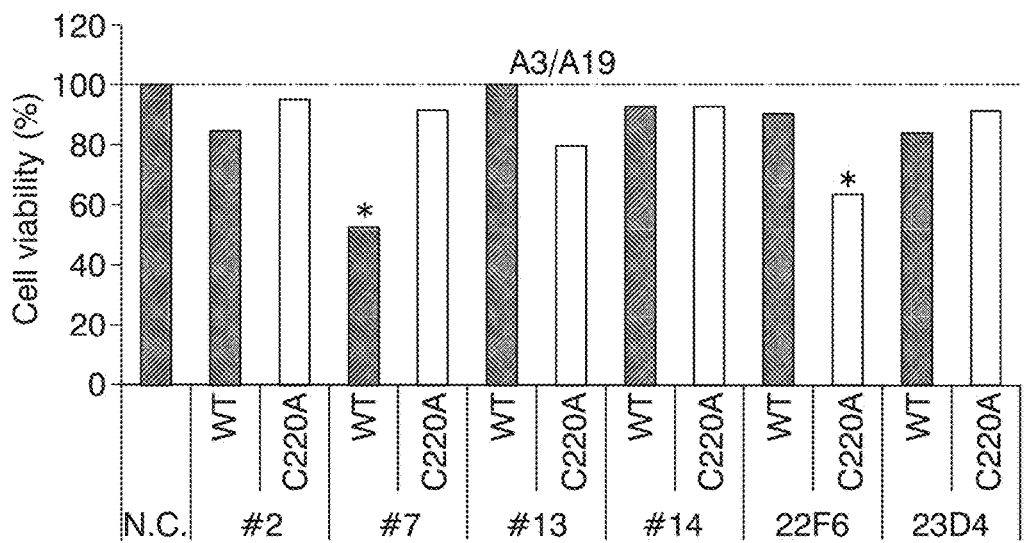
FIG. 5 is a graph indicating the results of investigating the cytotoxicity of various clones against cancer cells.

Cell viability at 24 hours and 48 hours after adding human antibody κ-type light chain is shown in FIG. 4, FIG. 5, Table 1 and Table 2 for each of the human antibody κ-type light chains. The results for the clones having a germline genotype of A18b or 011/ol are shown in FIG. 4 and Table 1, and the results for the clones having a germline genotype of A3/A19 are shown in FIG. 5 and Table 2. In addition, Tables 1 and 2 also indicate the concentrations of the human antibody κ-type light chains in the wells.

TABLE 1

| Clone | Concentration in well (µM) | Cell viability (%) | |
|---|---|---|---|
| | | After 24 hr | After 48 hr |
| #1_WT | 44 | 60 | 60 |
| #1 C220A | 40 | 72 | 75 |
| #8 WT | 29 | 79 | 81 |
| #8 C220A | 38 | 96 | 93 |
| #9 WT | 20 | 78 | 75 |
| #9 C220A | 40 | 86 | 84 |
| #11 WT | 28 | 73 | 80 |
| #11 C220A | 44 | 95 | 94 |

TABLE 1-continued

| Clone | Concentration in well (μM) | Cell viability (%) After 24 hr | After 48 hr |
|---|---|---|---|
| #4 WT | 20 | 50 | 54 |
| #4 C220A | 44 | 96 | 93 |

TABLE 2

| Clone | Concentration in well (μM) | Cell viability (%) After 24 hr | After 48 hr |
|---|---|---|---|
| #2 WT | 27 | 81 | 86 |
| #2 C220A | 40 | 94 | 95 |
| #7 WT | 35 | 49 | 53 |
| #7 C220A | 40 | 92 | 93 |
| #13 WT | 40 | 101 | 101 |
| #13 C220A | 56 | 97 | 81 |
| #14 WT | 32 | 100 | 94 |
| #14 C220A | 40 | 89 | 88 |
| 22F6 WT | 62 | 80 | 92 |
| 22F6 C220A | 32 | 65 | 64 |
| 23D4 WT | 28 | 83 | 85 |
| 23D4 C220A | 44 | 96 | 92 |

As a result, the four clones consisting of clone (#1_WT), clone (#4_WT), clone (#7 WT) and clone (22F6_C220A) demonstrated cytotoxicity on the order of 40% to 50% against A549 cells. Other clones were observed to hardly demonstrate any cytotoxicity against A549 cells.

Among these four clones, clone (#4_WT) and clone (#7_WT) demonstrated particularly potent cytotoxicity. Among these, clone (#7_WT), namely, human antibody κ-type light chain (#7), was suggested to have an effect that suppresses proliferation of A549 cells since there were hardly any changes in the number of cells in the wells between prior to addition of the human antibody κ-type light chain (0 hours) and after addition of the human antibody κ-type light chain (48 hours).

In addition, on the basis of the results for the clones used in this test, potent cytotoxicity was suggested to be present in dimers since it was observed that dimers (WT) have a tendency to demonstrate more potent cytotoxicity than monomers.

In addition, cytotoxicity of human antibody κ-type light chain against various cell lines was evaluated in the same manner as described above while also including other clones. Those results are shown in Table 3.

TABLE 3

| Cell type | Clone | Cell viability (%) 24 hr after addition | 48 hr after addition |
|---|---|---|---|
| A549 | #1 H31Y C220A | 72 | 53 |
|  | #7 VL(I) | 77 | 82 |
|  | #7 RLI | 74 | 90 |
|  | C51 | 78 | 87 |
|  | C87 | 75 | 65 |
| MOLT-4 | #1 H31Y C220A | 57.1 | 60.2 |
|  | #4 wt | 73.8 | 90.6 |
|  | #7 EI | 87 | 80.2 |
|  | #7 TR | 93.2 | 74.1 |
|  | #7 RLI | 55 | 73 |
|  | #7 VL | 77.3 | 84.2 |
|  | S13 | 75.3 | 108 |
|  | S21 | 78.2 | 91.3 |
|  | S38 | 77.3 | 85.5 |
|  | C51 | 59.4 | 63 |
| ES-2 | #1 H31Y C220A | 59.9 | 72.7 |
|  | #4 | 83.9 | 93.3 |
|  | #7 wt | 98.3 | 98.6 |
|  | #7 RLI | 100 | 94.8 |
|  | #10 | 79.9 | 92.4 |
|  | #11 | 57 | 78.8 |
|  | 22F6 | 63.1 | 89 |
|  | 22F6 C220A | 53.2 | 67.4 |
|  | C51 | 71.2 | 70.7 |
|  | C67 | 69.7 | 76.1 |
|  | C82 | 62.2 | 72.7 |
|  | C88 | 78.1 | 76.6 |
| BxPC | #4 | 58 | 63.3 |
|  | #7 G | 88.3 | 71.9 |
|  | #7 EI | 80.5 | 69.9 |
|  | #7 RLI | 87.9 | 77.3 |
|  | #7 VL | 77.7 | 75.9 |
|  | #13 | 120.4 | 67.6 |
|  | #14 | 116.6 | 69.3 |
|  | 22F6 | 115.2 | 65.5 |
| B-16 | #7 wt | 85 | 92 |

As a result, clone (#1_H31Y C220A) demonstrated a high level of cytotoxicity against A549 cells, MOLT-4 cells and ES-2 cells. In addition, clone (#7 RLI) and clone (C51) demonstrated a high level of cytotoxicity against MOLT-4 cells. Moreover, clone (#4) demonstrated a high level of cytotoxicity against ES-2 cells.

Furthermore, the amino acid sequence of clone (#1_H31Y C220A) is shown in SEQ ID NO: 38, the amino acid sequence of clone (#7 VL(I)) is shown in SEQ ID NO: 39, the amino acid sequence of clone (#7 RLI) is shown in SEQ ID NO: 40, the amino acid sequence of clone (C51) is shown in SEQ ID NO: 41, the amino acid sequence of clone (C87) is shown in SEQ ID NO: 42, the amino acid sequence of clone (#7 EI) is shown in SEQ ID NO: 43, the amino acid sequence of clone (#7 TR) is shown in SEQ ID NO: 44, the amino acid sequence of clone (#7 VL) is shown in SEQ ID NO: 45, the amino acid sequence of clone (S13) is shown in SEQ ID NO: 46, the amino acid sequence of clone (S21) is shown in SEQ ID NO: 47, the amino acid sequence of clone (S38) is shown in SEQ ID NO: 48, the amino acid sequence of clone (#10) is shown in SEQ ID NO: 49, the amino acid sequence of clone (C67) is shown in SEQ ID NO: 50, the amino acid sequence of clone (C82) is shown in SEQ ID NO: 51, the amino acid sequence of clone (C88) is shown in SEQ ID NO: 52, and the amino acid sequence of clone (#7 G) is shown in SEQ ID NO: 53.

In addition, as shown in FIGS. 7 and 8, the anticancer agent containing the human antibody κ-type light chain of the present application did not demonstrate any toxicity in animal studies. FIG. 7 and FIG. 8 show the results of administering human antibody κ-type light chain of the present invention to animals and mice. FIG. 7A shows a condition of a single-dose oral administration study in animals. FIG. 7B shows the body weight change in animals in the single-dose oral administration study. FIG. 7C shows the macroscopic findings in animals in the single-dose oral administration study. FIG. 8A shows the toxicity study conducted in order to confirm the safety to human. FIG. 8B shows the body weight change in mice in the 7-day repeat-dose toxicity study (caudal vein). FIG. 8C shows the autopsy findings in mice in the 7-day repeat-dose toxicity study (caudal vein).

INDUSTRIAL APPLICABILITY

The present invention allows the development of a novel anticancer agent and the use thereof in the field of cancer treatment.

The invention claimed is:

1. A method of eradicating cancer cells or suppressing or inhibiting a proliferation of the cancer cells, comprising:
   administering a therapeutically effective amount of an anticancer composition to an object requiring an administration, the anticancer composition comprising:
   (5) a human antibody κ-type light chain in the form of a monomer in which a variable region is composed of a polypeptide of
   an amino acid sequence of SEQ ID NO: 19,
   an amino acid sequence having homology of 95% or more with the amino acid sequence of SEQ ID NO: 19 and having the same CDRs of the amino acid sequence of SEQ ID NO: 19,
   wherein the CDRs in the amino acid sequence of SEQ ID NO: 19 are the first 24 to 39 amino acid residues, the first 55 to 61 amino acid residues, and the first 94 to 101 amino acid residues.

2. A method of eradicating cancer cells or suppressing or inhibiting a proliferation of the cancer cells according to claim 1, wherein
   the human antibody κ-type light chain of (5) above is a human antibody κ-type light chain in the form of a monomer composed of a polypeptide of
   an amino acid sequence in which cysteine at position 219 has been deleted or substituted by an amino acid other than cysteine in the amino acid sequence of SEQ ID NO: 20,
   an amino acid sequence having homology of 95% or more with the amino acid sequence of SEQ ID NO: 20 and having the same CDRs of the amino acid sequence of SEQ ID NO: 20,
   wherein the CDRs in the amino acid sequence of SEQ ID NO: 20 are the first 24 to 39 amino acid residues, the first 55 to 61 amino acid residues, and the first 94 to 101 amino acid residues.

3. A method of eradicating cancer cells or suppressing or inhibiting a proliferation of the cancer cells according to claim 1, wherein the object requiring the administration has already developed lung cancer.

4. A method of eradicating cancer cells or suppressing or inhibiting a proliferation of the cancer cells according to claim 1, comprising: administrating the anticancer composition in a form which enables the anticancer composition to be delivered to pneumocytes from a nose or bronchi.

5. A method of eradicating cancer cells or suppressing or inhibiting a proliferation of the cancer cells according to claim 1, wherein protein contained in the anticancer composition is administered at a dose of 0.01 mg/kg to 30 mg/kg of body weight.

* * * * *

SEQUENCE LISTING

```
<160> NUMBER OF SEQ ID NOS: 56

<210> SEQ ID NO 1
<211> LENGTH: 113
<212> TYPE: PRT
<213> ORGANISM: human

<400> SEQUENCE: 1

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly His Ser
        35                  40                  45

Pro His Leu Leu Leu Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu His Leu Pro Gln Tyr Thr Phe Gly Gln Gly Thr Lys Leu Glu Ile
            100                 105                 110

Lys

<210> SEQ ID NO 2
<211> LENGTH: 220
<212> TYPE: PRT
<213> ORGANISM: human

<400> SEQUENCE: 2

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly His Ser
        35                  40                  45

Pro His Leu Leu Leu Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu His Leu Pro Gln Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
```

```
                165                 170                 175
Ser Thr Tyr Ser Leu Ser Ser Thr Leu Thr Leu Ser Lys Ala Asp Tyr
            180                 185                 190

Glu Lys His Lys Leu Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 3
<211> LENGTH: 112
<212> TYPE: PRT
<213> ORGANISM: human

<400> SEQUENCE: 3

Asp Val Val Met Thr Gln Thr Pro Leu Ser Leu Ser Val Thr Pro Gly
 1                5                  10                 15

Gln Pro Ala Ser Leu Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Glu Gly
                85                  90                  95

Thr His Leu Pro Trp Thr Phe Gly Gln Gly Thr Lys Val Glu Ile Lys
            100                 105                 110

<210> SEQ ID NO 4
<211> LENGTH: 219
<212> TYPE: PRT
<213> ORGANISM: human

<400> SEQUENCE: 4

Asp Val Val Met Thr Gln Thr Pro Leu Ser Leu Ser Val Thr Pro Gly
 1                5                  10                 15

Gln Pro Ala Ser Leu Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Glu Gly
                85                  90                  95

Thr His Leu Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
```

```
                165                 170                 175
Thr Tyr Ser Leu Ser Ser Thr Leu Thr Leu Ser Lys Ala Asp Tyr Glu
            180                 185                 190

Lys His Lys Leu Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 5
<211> LENGTH: 112
<212> TYPE: PRT
<213> ORGANISM: human

<400> SEQUENCE: 5

Asp Val Val Met Thr Gln Thr Pro Leu Ser Leu Ser Val Thr Pro Gly
  1               5                  10                  15

Gln Pro Ala Ser Ile Ser Cys Lys Ser Ser Gln Ser Leu Leu His Ser
             20                  25                  30

Asp Gly Lys Thr Tyr Leu Tyr Trp Tyr Leu Gln Lys Pro Gly Gln Ser
         35                  40                  45

Pro Gln Leu Leu Ile Tyr Glu Val Ser Ser Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Ile His Leu Pro Tyr Thr Phe Gly Gln Gly Thr Lys Leu Glu Ile Lys
            100                 105                 110

<210> SEQ ID NO 6
<211> LENGTH: 219
<212> TYPE: PRT
<213> ORGANISM: human

<400> SEQUENCE: 6

Asp Val Val Met Thr Gln Thr Pro Leu Ser Leu Ser Val Thr Pro Gly
  1               5                  10                  15

Gln Pro Ala Ser Ile Ser Cys Lys Ser Ser Gln Ser Leu Leu His Ser
             20                  25                  30

Asp Gly Lys Thr Tyr Leu Tyr Trp Tyr Leu Gln Lys Pro Gly Gln Ser
         35                  40                  45

Pro Gln Leu Leu Ile Tyr Glu Val Ser Ser Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Ile His Leu Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
```

```
                   165                 170                 175
Thr Tyr Ser Leu Ser Ser Thr Leu Thr Leu Ser Lys Ala Asp Tyr Glu
            180                 185                 190

Lys His Lys Leu Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 7
<211> LENGTH: 112
<212> TYPE: PRT
<213> ORGANISM: human

<400> SEQUENCE: 7

Asp Ile Val Met Thr Gln Thr Pro Leu Ser Leu Ser Val Thr Pro Gly
  1               5                  10                  15

Gln Pro Ala Ser Ile Ser Cys Lys Ser Ser Gln Ser Leu Leu His Ser
             20                  25                  30

Asp Gly Lys Thr Tyr Leu Tyr Trp Tyr Leu Gln Lys Pro Gly Gln Ser
         35                  40                  45

Pro Gln Leu Leu Leu Tyr Glu Val Ser Ser Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Ile His Leu Pro Tyr Thr Phe Gly Gln Gly Thr Lys Leu Glu Ile Lys
            100                 105                 110

<210> SEQ ID NO 8
<211> LENGTH: 219
<212> TYPE: PRT
<213> ORGANISM: human

<400> SEQUENCE: 8

Asp Ile Val Met Thr Gln Thr Pro Leu Ser Leu Ser Val Thr Pro Gly
  1               5                  10                  15

Gln Pro Ala Ser Ile Ser Cys Lys Ser Ser Gln Ser Leu Leu His Ser
             20                  25                  30

Asp Gly Lys Thr Tyr Leu Tyr Trp Tyr Leu Gln Lys Pro Gly Gln Ser
         35                  40                  45

Pro Gln Leu Leu Leu Tyr Glu Val Ser Ser Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Ile His Leu Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
```

```
                  165                 170                 175
Thr Tyr Ser Leu Ser Ser Thr Leu Thr Leu Ser Lys Ala Asp Tyr Glu
        180                 185                 190
Lys His Lys Leu Tyr Ala Cys Glu Val Thr His Gln Gly Leu Ser Ser
        195                 200                 205
Pro Val Thr Lys Ser Phe Asn Arg Gly Glu Cys
        210                 215

<210> SEQ ID NO 9
<211> LENGTH: 113
<212> TYPE: PRT
<213> ORGANISM: human

<400> SEQUENCE: 9

Asp Val Val Met Thr Gln Thr Pro Leu Ser Leu Ser Val Thr Pro Gly
 1               5                  10                  15
Glu Pro Ala Ser Ile Ser Cys Arg Ser Thr Gln Ser Leu Leu Asp Ser
            20                  25                  30
Asp Gly Val Asn Pro Ser Phe Asp Trp Tyr Val Gln Lys Pro Gly Gln
        35                  40                  45
Ser Pro Gln Leu Leu Ile His Arg Gly Phe Tyr Arg Ala Ser Gly Val
    50                  55                  60
Pro Asp Arg Phe Ser Gly Ser Gly Ser Gly Thr Asp Phe Thr Leu Arg
65                  70                  75                  80
Ile Ser Arg Val Glu Ala Glu Asp Val Gly Val Tyr Tyr Cys Met Gln
                85                  90                  95
Arg Ile Glu Phe Pro Leu Thr Phe Gly Gly Gly Thr Lys Val Glu Leu
            100                 105                 110
Lys

<210> SEQ ID NO 10
<211> LENGTH: 220
<212> TYPE: PRT
<213> ORGANISM: human

<400> SEQUENCE: 10

Asp Val Val Met Thr Gln Thr Pro Leu Ser Leu Ser Val Thr Pro Gly
 1               5                  10                  15
Glu Pro Ala Ser Ile Ser Cys Arg Ser Thr Gln Ser Leu Leu Asp Ser
            20                  25                  30
Asp Gly Val Asn Pro Ser Phe Asp Trp Tyr Val Gln Lys Pro Gly Gln
        35                  40                  45
Ser Pro Gln Leu Leu Ile His Arg Gly Phe Tyr Arg Ala Ser Gly Val
    50                  55                  60
Pro Asp Arg Phe Ser Gly Ser Gly Ser Gly Thr Asp Phe Thr Leu Arg
65                  70                  75                  80
Ile Ser Arg Val Glu Ala Glu Asp Val Gly Val Tyr Tyr Cys Met Gln
                85                  90                  95
Arg Ile Glu Phe Pro Leu Thr Phe Gly Gly Gly Thr Lys Val Glu Leu
            100                 105                 110
Lys Arg Thr Val Ala Ala Pro Ser Val Phe Ile Phe Pro Pro Ser Asp
        115                 120                 125
Glu Gln Leu Lys Ser Gly Thr Ala Ser Val Val Cys Leu Leu Asn Asn
    130                 135                 140
Phe Tyr Pro Arg Glu Ala Lys Val Gln Trp Lys Val Asp Asn Ala Leu
145                 150                 155                 160
```

```
Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
        180                 185                 190

Glu Lys His Lys Leu Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 11
<211> LENGTH: 112
<212> TYPE: PRT
<213> ORGANISM: human

<400> SEQUENCE: 11

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Gly
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Ile Arg Ala Ser Gly Val Pro
    50                  55                  60

Asp Arg Phe Ser Gly Ser Gly Ser Gly Thr Asp Phe Gln Leu Lys Ile
65                  70                  75                  80

Ser Arg Val Glu Ala Asp Asp Val Gly Ile Tyr Tyr Cys Met Gln Ala
                85                  90                  95

Gln Gln Gly Pro Pro Thr Phe Gly Gly Gly Thr Lys Val Glu Ile Lys
            100                 105                 110

<210> SEQ ID NO 12
<211> LENGTH: 219
<212> TYPE: PRT
<213> ORGANISM: human

<400> SEQUENCE: 12

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Gly
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Ile Arg Ala Ser Gly Val Pro
    50                  55                  60

Asp Arg Phe Ser Gly Ser Gly Ser Gly Thr Asp Phe Gln Leu Lys Ile
65                  70                  75                  80

Ser Arg Val Glu Ala Asp Asp Val Gly Ile Tyr Tyr Cys Met Gln Ala
                85                  90                  95

Gln Gln Gly Pro Pro Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160
```

```
Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Leu Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 13
<211> LENGTH: 112
<212> TYPE: PRT
<213> ORGANISM: human

<400> SEQUENCE: 13

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110

<210> SEQ ID NO 14
<211> LENGTH: 219
<212> TYPE: PRT
<213> ORGANISM: human

<400> SEQUENCE: 14

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160
```

```
Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Leu Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 15
<211> LENGTH: 113
<212> TYPE: PRT
<213> ORGANISM: human

<400> SEQUENCE: 15

Asp Val Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Pro Trp Thr Phe Gly Gln Gly Thr Lys Val Glu Ile
            100                 105                 110

Lys

<210> SEQ ID NO 16
<211> LENGTH: 220
<212> TYPE: PRT
<213> ORGANISM: human

<400> SEQUENCE: 16

Asp Val Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140
```

```
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
        180                 185                 190

Glu Lys His Lys Leu Tyr Ala Cys Glu Val Thr His Gln Gly Leu Ser
        195                 200                 205

Ser Pro Val Thr Lys Ser Phe Asn Arg Gly Glu Cys
        210                 215                 220
```

<210> SEQ ID NO 17
<211> LENGTH: 112
<212> TYPE: PRT
<213> ORGANISM: human

<400> SEQUENCE: 17

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Leu Glu Ile Lys
            100                 105                 110
```

<210> SEQ ID NO 18
<211> LENGTH: 219
<212> TYPE: PRT
<213> ORGANISM: human

<400> SEQUENCE: 18

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140
```

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Leu Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 19
<211> LENGTH: 112
<212> TYPE: PRT
<213> ORGANISM: human

<400> SEQUENCE: 19

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Phe Asn Tyr Leu Asp Trp Tyr Leu Gln Lys Pro Gly Gln Ser
        35                  40                  45

Pro Gln Leu Leu Ile Tyr Leu Gly Ser Thr Arg Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Phe Cys Met Gln Ala
                85                  90                  95

Val Gln Thr Pro Phe Thr Phe Gly Pro Gly Thr Arg Leu Asp Ile Lys
            100                 105                 110

<210> SEQ ID NO 20
<211> LENGTH: 219
<212> TYPE: PRT
<213> ORGANISM: human

<400> SEQUENCE: 20

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Phe Asn Tyr Leu Asp Trp Tyr Leu Gln Lys Pro Gly Gln Ser
        35                  40                  45

Pro Gln Leu Leu Ile Tyr Leu Gly Ser Thr Arg Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Phe Cys Met Gln Ala
                85                  90                  95

Val Gln Thr Pro Phe Thr Phe Gly Pro Gly Thr Arg Leu Asp Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

```
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215
```

<210> SEQ ID NO 21
<211> LENGTH: 112
<212> TYPE: PRT
<213> ORGANISM: human

<400> SEQUENCE: 21

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110
```

<210> SEQ ID NO 22
<211> LENGTH: 219
<212> TYPE: PRT
<213> ORGANISM: human

<400> SEQUENCE: 22

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140
```

```
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence:Artificially
      Synthesized Sequence

<400> SEQUENCE: 23

```
Leu Glu His His His His His His
 1               5
```

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence:Artificially
      Synthesized Seqence

<400> SEQUENCE: 24
ctcgagcacc accaccacca ccactga                                          27

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence:Artificially
      Synthesized Sequence

<400> SEQUENCE: 25

```
Ala Leu Glu His His His His His His
 1               5
```

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized Seqence

<400> SEQUENCE: 26
gctctcgagc accaccacca ccaccactga                                       30

<210> SEQ ID NO 27
<211> LENGTH: 660
<212> TYPE: DNA
<213> ORGANISM: human

<400> SEQUENCE: 27
gatattgtga tgacccagac tccactctct ctgtccgtca cccctggaca gccggcctcc     60

| | |
|---|---|
| atctcctgca agtctagtca gagcctcctg catagtgatg gaaagaccta tttgtattgg | 120 |
| tacctgcaga agccaggcca ctctccacat ctcctaatct atgaggtttc cagccggttc | 180 |
| tctggagtgc cagataggtt cagtggcagc gggtcaggga cagatttcac actgaaaatc | 240 |
| agccgggtgg aggctgagga tgttgggggtt tattactgca tgcaaggttt acaccttcct | 300 |
| cagtacactt ttggccaggg gaccaagctg gagatcaaac gaactgtggc tgcaccatct | 360 |
| gtcttcatct cccgccatc tgatgagcag ttgaaatctg gaactgcctc tgttgtgtgc | 420 |
| ctgctgaata acttctatcc cagagaggcc aaagtacagt ggaaggtgga taacgccctc | 480 |
| caatcgggta actcccagga gagtgtcaca gagcaggaca gcaaggacag cacctacagc | 540 |
| ctcagcagca ccctgacgct gagcaaagca gactacgaga aacacaaact ctacgcctgc | 600 |
| gaagtcaccc atcagggcct gagctcgccc gtcacaaaga gcttcaacag gggagagtgt | 660 |

<210> SEQ ID NO 28
<211> LENGTH: 657
<212> TYPE: DNA
<213> ORGANISM: human

<400> SEQUENCE: 28

| | |
|---|---|
| gatgttgtga tgacccagac tccactctct ctgtccgtca cccctgggca gccggcctcc | 60 |
| ctctcctgca gtctagtca gagcctcctg catagtgatg gaaagaccta tttgtattgg | 120 |
| tacctgcaga agccaggcca gtctccacaa ctcctaatct atgaagtttc cagccggttc | 180 |
| tctggagtgc cagataggtt cagtggcagc gggtcaggga cagatttcac actgaaaatc | 240 |
| agccgcgtgg aggctgagga tgttggagtt tattactgta tggaaggtac acaccttccg | 300 |
| tggacgttcg gccaagggac caaggtggaa atcaaacgaa ctgtggctgc accatctgtc | 360 |
| ttcatcttcc cgccatctga tgagcagttg aaatctggaa ctgcctctgt tgtgtgcctg | 420 |
| ctgaataact tctatcccag agaggccaaa gtacagtgga aggtggataa cgccctccaa | 480 |
| tcgggtaact cccaggagag tgtcacagag caggacagca aggacagcac ctacagcctc | 540 |
| agcagcaccc tgacgctgag caaagcagac tacgagaaac acaaactcta cgcctgcgaa | 600 |
| gtcacccatc agggcctgag ctcgcccgtc acaaagagct tcaacagggg agagtgt | 657 |

<210> SEQ ID NO 29
<211> LENGTH: 657
<212> TYPE: DNA
<213> ORGANISM: human

<400> SEQUENCE: 29

| | |
|---|---|
| gatgttgtga tgacccagac tccactctct ctgtccgtca cccctggaca gccggcctcc | 60 |
| atctcctgca gtctagtca gagcctcctg catagtgatg gaaagaccta tttgtattgg | 120 |
| tacctgcaga agccaggcca gtctccacag ctcctaatct atgaagtttc cagccggttc | 180 |
| tctggagtgc cagataggtt cagtggcagc gggtcaggga cagatttcac actgaaaatc | 240 |
| agccgggtgg aggctgagga tgttgggggtt tattactgca tgcaaggtat acaccttccg | 300 |
| tacactttg gccaggggac caagctggag atcaaacgaa ctgtggctgc accatctgtc | 360 |
| ttcatcttcc cgccatctga tgagcagttg aaatctggaa ctgcctctgt tgtgtgcctg | 420 |
| ctgaataact tctatcccag agaggccaaa gtacagtgga aggtggataa cgccctccaa | 480 |
| tcgggtaact cccaggagag tgtcacagag caggacagca aggacagcac ctacagcctc | 540 |
| agcagcaccc tgacgctgag caaagcagac tacgagaaac acaaactcta cgcctgcgaa | 600 |
| gtcacccatc agggcctgag ctcgcccgtc acaaagagct tcaacagggg agagtgt | 657 |

<210> SEQ ID NO 30
<211> LENGTH: 657
<212> TYPE: DNA
<213> ORGANISM: human

<400> SEQUENCE: 30

```
gatattgtga tgacccagac tccactctct ctgtccgtca cccctggaca gccggcctcc      60
atctcctgca agtctagtca gagcctcctg catagtgatg aaagaccta tttgtattgg     120
tacctgcaga agccaggcca gtctccacag ctcctaatct atgaagtttc agccggttc     180
tctggagtgc cagataggtt cagtggcagc gggtcaggga cagatttcac actgaaaatc    240
agccgggtgg aggctgagga tgttggggtt tattactgca tgcaaggtat acaccttccg    300
tacactttg gccaggggac caagctggag atcaaacgaa ctgtggctgc accatctgtc     360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaactcta cgcctgcgaa    600
gtcacccatc agggcctgag ctcgcccgtc acaaagagct caacagggg agagtgt       657
```

<210> SEQ ID NO 31
<211> LENGTH: 660
<212> TYPE: DNA
<213> ORGANISM: human

<400> SEQUENCE: 31

```
gatgttgtga tgacccagac tccactctcc ctgtccgtca cccctggaga gccggcctcc     60
atctcctgca ggtctactca gagcctcttg gatagtgatg gtgtaaaccc ctctttcgac    120
tggtatgtac agaagccagg gcagtctcca caactcctga ttcatagagg tttctatcgg    180
gcctctggag tcccagacag gttcagtggc agtgggtcag gcactgattt cacactgagg    240
atcagcaggg tggaggctga ggatgttgga gtctattact gcatgcaacg catagagttt    300
cctctcactt tcggcggagg gaccaaggtg gagatcaagc gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaaact ctacgcctgc    600
gaagtcaccc atcagggcct gagctcgccc gtcacaaaga gcttcaacag gggagagtgt    660
```

<210> SEQ ID NO 32
<211> LENGTH: 657
<212> TYPE: DNA
<213> ORGANISM: human

<400> SEQUENCE: 32

```
gatgttgtga tgactcagtc tccactctcc ctgcccgtca cccctggaga gccggcctcc     60
atctcctgca ggtctagtca gagcctcctg tatgggaatg aaacaactta tttggattgg    120
tacctgcaga agccaggaca gtctccacag ctcctgatct atttgggttc tattcgggcc    180
tccggggtcc ctgacaggtt cagtggcagt ggatcaggca cagatttcca actgaaaatc    240
agcagagtgg aggctgacga tgttgggatt tattactgca tgcaagctca acaaggtccg    300
```

```
cccactttcg gcggagggac caaggtggag atcaaacgaa ctgtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaactcta cgcctgcgaa    600
gtcacccatc agggcctgag ctcgcccgtc acaaagagct caacagggg agagtgt       657
```

<210> SEQ ID NO 33
<211> LENGTH: 657
<212> TYPE: DNA
<213> ORGANISM: human

<400> SEQUENCE: 33

```
gatgttgtga tgactcagtc tccactctcc ctgcccgtca cccctggaga gccggcctcc     60
atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactcct    300
cgtacgttcg gccaagggac caaggtggaa atcaaacgaa ctgtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaactcta cgcctgcgaa    600
gtcacccatc agggcctgag ctcgcccgtc acaaagagct caacagggg agagtgt       657
```

<210> SEQ ID NO 34
<211> LENGTH: 660
<212> TYPE: DNA
<213> ORGANISM: human

<400> SEQUENCE: 34

```
gatgttgtga tgactcagtc tccactctcc ctgcccgtca cccctggaga gccggcctcc     60
atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactcct    300
ccgtggacgt tcggccaagg gaccaaggtg gaaatcaaac gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaaact ctacgcctgc    600
gaagtcaccc atcagggcct gagctcgccc gtcacaaaga gcttcaacag gggagagtgt    660
```

<210> SEQ ID NO 35
<211> LENGTH: 657
<212> TYPE: DNA
<213> ORGANISM: human

<400> SEQUENCE: 35

```
gatattgtga tgactcagtc tccactctcc ctgcccgtca cccctggaga gccggcctcc    60
atctcctgca ggtctagtca gagcctcctg catagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcaagctct acaaactcct   300 cggactttg gccaggggac caagctggag atcaaacgaa ctgtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaactcta cgcctgcgaa   600
gtcacccatc agggcctgag ctcgcccgtc acaaagagct tcaacagggg agagtgt     657
```

<210> SEQ ID NO 36
<211> LENGTH: 657
<212> TYPE: DNA
<213> ORGANISM: human

<400> SEQUENCE: 36

```
gatattgtga tgactcagtc tccactctcc ctgcccgtca cccctggaga gccggcctcc    60
atctcctgca ggtctagtca gagcctcctg catagtaatg gattcaacta tttggattgg   120
tatctgcaga agccagggca gtctccacag ctcctgatct atttgggttc tactcgggcc   180
tccggggtcc ctgacaggtt cagtggcagt ggatcaggca cagattttac actgagaatc   240
agcagagtgg aggctgagga tgttggggtt tatttctgca tgcaagctgt ccaaactcct   300
ttcactttcg gccctgggac cagactggat atcaaacgaa ctgtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgt     657
```

<210> SEQ ID NO 37
<211> LENGTH: 657
<212> TYPE: DNA
<213> ORGANISM: human

<400> SEQUENCE: 37

```
gatattgtga tgactcagtc tccactctcc ctgcccgtca cccctggaga gccggcctcc    60
atctcctgca ggtctagtca gagcctcctg catagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcaagctct acaaactccc   300
tggacgttcg gccaagggac caaggtggaa atcaaacgaa ctgtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
```

-continued

```
agcagcaccc tgacgctgag caaagcagac tacgagaaac acaaagtcta cgcctgcgaa        600
gtcacccatc agggcctgag ctcgcccgtc acaaagagct tcaacagggg agagtgt           657
```

<210> SEQ ID NO 38
<211> LENGTH: 220
<212> TYPE: PRT
<213> ORGANISM: human

<400> SEQUENCE: 38

```
Asp Val Val Met Thr Gln Thr Pro Leu Ser Leu Ser Val Thr Pro Gly
  1               5                  10                  15

Gln Pro Ala Ser Ile Ser Cys Lys Ser Ser Gln Ser Leu Leu Tyr Ser
             20                  25                  30

Asp Gly Lys Thr Tyr Leu Tyr Trp Tyr Leu Gln Lys Pro Gly His Ser
         35                  40                  45

Pro His Leu Leu Ile Tyr Glu Val Ser Ser Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Leu His Leu Pro Gln Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Leu Tyr Ala Cys Glu Val Thr His Gln Gly Leu Ser
        195                 200                 205

Ser Pro Val Thr Lys Ser Phe Asn Arg Gly Glu Ala
    210                 215                 220
```

<210> SEQ ID NO 39
<211> LENGTH: 219
<212> TYPE: PRT
<213> ORGANISM: human

<400> SEQUENCE: 39

```
Glu Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Thr Arg Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95
```

```
Leu Gln Thr Pro Ile Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Leu Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 40
<211> LENGTH: 219
<212> TYPE: PRT
<213> ORGANISM: human

<400> SEQUENCE: 40

Glu Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Thr Arg Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Gln Thr Pro Ile Thr Phe Gly Gln Gly Thr Arg Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Leu Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 41
<211> LENGTH: 214
<212> TYPE: PRT
```

<213> ORGANISM: human

<400> SEQUENCE: 41

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Thr Ser Leu Glu Pro
65                  70                  75                  80

Glu Asp Phe Ala Val Tyr Tyr Cys Gln Gln Arg Ser Asp Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 42
<211> LENGTH: 213
<212> TYPE: PRT
<213> ORGANISM: human

<400> SEQUENCE: 42

Glu Ile Val Leu Thr Gln Ser Pro Ala Thr Leu Ser Leu Ser Pro Gly
1               5                   10                  15

Glu Arg Ala Thr Phe Ser Cys Arg Ala Ser Gln Ser Leu Ser Ser Tyr
            20                  25                  30

Val Ala Trp Tyr Gln Lys Lys Pro Gly Gln Ala Pro Arg Leu Leu Ile
        35                  40                  45

Tyr Asp Thr Ser Thr Arg Ala Ala Gly Ile Pro Ala Arg Phe Ser Gly
    50                  55                  60

Gly Gly Ser Gly Thr Asp Phe Thr Leu Thr Ile Ser Ser Leu Glu Pro
65                  70                  75                  80

Glu Asp Cys Ala Val Tyr Tyr Cys Gln Arg Arg Ala Thr Pro Tyr Thr
                85                  90                  95

Phe Gly Gln Gly Thr Arg Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys

```
                    130                 135                 140
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Arg Val Tyr Ala
            180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 43
<211> LENGTH: 219
<212> TYPE: PRT
<213> ORGANISM: human

<400> SEQUENCE: 43

Glu Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Leu Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 44
<211> LENGTH: 219
<212> TYPE: PRT
<213> ORGANISM: human

<400> SEQUENCE: 44

Asp Val Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
```

```
                    20                  25                  30
Asn Thr Arg Asn Tyr Leu Asp Trp Tyr Leu Gln Lys Pro Gly Gln Ser
                35                  40                  45
Pro Gln Leu Leu Ile Tyr Leu Gly Ser Asn Arg Ala Ser Gly Val Pro
         50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Met Gln Ala
                 85                  90                  95
Leu Gln Thr Pro Arg Thr Phe Gly Gln Gly Thr Lys Val Glu Ile Lys
                100                 105                 110
Arg Thr Val Ala Ala Pro Ser Val Phe Ile Phe Pro Pro Ser Asp Glu
                115                 120                 125
Gln Leu Lys Ser Gly Thr Ala Ser Val Val Cys Leu Leu Asn Asn Phe
            130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
                180                 185                 190
Lys His Lys Leu Tyr Ala Cys Glu Val Thr His Gln Gly Leu Ser Ser
            195                 200                 205
Pro Val Thr Lys Ser Phe Asn Arg Gly Glu Cys
        210                 215

<210> SEQ ID NO 45
<211> LENGTH: 219
<212> TYPE: PRT
<213> ORGANISM: human

<400> SEQUENCE: 45

Glu Ile Val Met Thr Gln Ser Pro Leu Ser Leu Pro Val Thr Pro Gly
  1               5                  10                  15
Glu Pro Ala Ser Ile Ser Cys Arg Ser Ser Gln Ser Leu Leu His Ser
                 20                  25                  30
Asn Thr Arg Asn Tyr Leu Asp Trp Tyr Leu Gln Lys Pro Gly Gln Ser
                35                  40                  45
Pro Gln Leu Leu Ile Tyr Leu Gly Ser Asn Arg Ala Ser Gly Val Pro
         50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Met Gln Gly
                 85                  90                  95
Leu Gln Thr Pro Arg Thr Phe Gly Gln Gly Thr Lys Val Glu Ile Lys
                100                 105                 110
Arg Thr Val Ala Ala Pro Ser Val Phe Ile Phe Pro Pro Ser Asp Glu
                115                 120                 125
Gln Leu Lys Ser Gly Thr Ala Ser Val Val Cys Leu Leu Asn Asn Phe
            130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
```

Thr Tyr Ser Leu Ser Ser Thr Leu Thr Leu Ser Lys Ala Asp Tyr Glu
            180                 185                 190

Lys His Lys Leu Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 46
<211> LENGTH: 219
<212> TYPE: PRT
<213> ORGANISM: human

<400> SEQUENCE: 46

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Ser Val Glu Ala Glu Asp Val Gly Val Tyr Tyr Cys Met Gln Ala
                85                  90                  95

Leu Glu Thr Pro Pro Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 47
<211> LENGTH: 219
<212> TYPE: PRT
<213> ORGANISM: human

<400> SEQUENCE: 47

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Arg Thr Phe Gly Pro Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 48
<211> LENGTH: 218
<212> TYPE: PRT
<213> ORGANISM: human

<400> SEQUENCE: 48

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 49
<211> LENGTH: 219
<212> TYPE: PRT
<213> ORGANISM: human

<400> SEQUENCE: 49

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Phe Tyr Trp Tyr Leu Gln Arg Pro Gly Arg Ser
        35                  40                  45

Pro Gln Leu Leu Ile Gln Glu Val Ser Arg Arg Phe Ser Gly Val Pro
    50                  55                  60

Asp Arg Phe Ser Gly Ser Gly Ser Gly Ser Asp Phe Thr Leu Lys Ile
65                  70                  75                  80

Ser Arg Val Glu Ala Glu Asp Val Gly Val Tyr Tyr Cys Met Gln Gly
                85                  90                  95

Thr Tyr Val Pro His Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Leu Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 50
<211> LENGTH: 215
<212> TYPE: PRT
<213> ORGANISM: human

<400> SEQUENCE: 50

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Asn Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Tyr Thr Leu Thr Ile Ser Arg Leu Glu
65                  70                  75                  80

Pro Glu Asp Phe Ala Leu Tyr Tyr Cys Gln Gln Tyr Gly Ser Ser Leu
                85                  90                  95

Trp Thr Phe Gly Gln Gly Thr Lys Val Glu Ile Lys Arg Thr Val Ala
            100                 105                 110

```
Ala Pro Ser Val Phe Ile Phe Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 51
<211> LENGTH: 215
<212> TYPE: PRT
<213> ORGANISM: human

<400> SEQUENCE: 51

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Gly Pro Phe
            20                  25                  30

Leu Ala Trp Tyr Gln Gln Lys Pro Gly Gln Ala Pro Arg Leu Leu Ile
        35                  40                  45

Tyr Asp Thr Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Tyr Thr Trp Pro Gly
                85                  90                  95

Asn Ser Phe Gly Gly Gly Ala Lys Val Glu Ile Lys Arg Thr Val Ala
            100                 105                 110

Ala Pro Ser Val Phe Ile Phe Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 52
<211> LENGTH: 216
<212> TYPE: PRT
<213> ORGANISM: human

<400> SEQUENCE: 52
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Ser Gly Tyr
            20                  25                  30

Leu Ala Trp Tyr Gln Gln Lys Pro Gly Gln Ala Pro Arg Leu Leu Ile
        35                  40                  45

Tyr Glu Ala Ser Asn Arg Ala Thr Gly Ile Pro Ala Arg Phe Ser Gly
    50                  55                  60

Ser Gly Ser Gly Pro Asp Phe Thr Leu Thr Ile Ser Ser Leu Glu Pro
65                  70                  75                  80

Glu Asp Phe Ala Phe Tyr Tyr Cys Gln Gln Arg Ser Asn Trp Pro Pro
                85                  90                  95

Arg Ser Thr Phe Gly Gln Gly Thr Arg Leu Glu Met Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
210                 215

<210> SEQ ID NO 53
<211> LENGTH: 219
<212> TYPE: PRT
<213> ORGANISM: human

<400> SEQUENCE: 53

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Gln Thr Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln

```
                145                 150                 155                 160
Ser Gly Asn Ser Gln Glu Ser Val Thr Glu Gln Asp Ser Lys Asp Ser
                    165                 170                 175

Thr Tyr Ser Leu Ser Ser Thr Leu Thr Leu Ser Lys Ala Asp Tyr Glu
                180                 185                 190

Lys His Lys Leu Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 54
<211> LENGTH: 219
<212> TYPE: PRT
<213> ORGANISM: human

<400> SEQUENCE: 54

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
                20                  25                  30

Asn Gly Phe Asn Tyr Leu Asp Trp Tyr Leu Gln Lys Pro Gly Gln Ser
            35                  40                  45

Pro Gln Leu Leu Ile Tyr Leu Gly Ser Thr Arg Ala Ser Gly Val Pro
        50                  55                  60

Asp Arg Phe Ser Gly Ser Gly Ser Gly Thr Asp Phe Thr Leu Arg Ile
 65                  70                  75                  80

Ser Arg Val Glu Ala Glu Asp Val Gly Val Tyr Phe Cys Met Gln Ala
                 85                  90                  95

Val Gln Thr Pro Phe Thr Phe Gly Pro Gly Thr Arg Leu Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                    165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Ala
        210                 215

<210> SEQ ID NO 55
<211> LENGTH: 66
<212> TYPE: DNA
<213> ORGANISM: Artificial Sequence
<220> FEATURE:
<223> OTHER INFORMATION: Description: Artificially Synthesized Seqence

<400> SEQUENCE: 55
gtcacaaaga gcttcaacag gggagagtgt ctcgagcacc accaccacca ccactgagat    60
ccggct                                                              66
```

```
<210> SEQ ID NO 56
<211> LENGTH: 66
<212> TYPE: DNA
<213> ORGANISM: Artificial Sequence
<220> FEATURE:
<223> OTHER INFORMATION: Description: Artificially Synthesized Seqence

<400> SEQUENCE: 56
gtcacaaaga gcttcaacag gggagaggct ctcgagcacc accaccacca ccactgagat      60
ccggct                                                                66
```